United States Patent [19]
Ritter et al.

[11] Patent Number: 6,086,863
[45] Date of Patent: *Jul. 11, 2000

[54] COMPOSITIONS OF MICROSPHERES FOR WOUND HEALING

[75] Inventors: Vladimir Ritter; Marina Ritter, both of Kiriat-Yam, Israel

[73] Assignee: Polyheal Ltd., Haifa, Israel

[*] Notice: This patent issued on a continued prosecution application filed under 37 CFR 1.53(d), and is subject to the twenty year patent term provisions of 35 U.S.C. 154(a)(2).

[21] Appl. No.: 09/177,954

[22] Filed: Oct. 23, 1998

Related U.S. Application Data

[63] Continuation-in-part of application No. 08/868,950, Jun. 4, 1997, Pat. No. 5,861,149.

[51] Int. Cl.[7] .................................................. A61K 31/74
[52] U.S. Cl. .................................. 424/78.06; 424/78.06; 424/69; 514/62; 514/58; 522/7; 623/11; 29/407
[58] Field of Search ................... 424/78.06, 69; 514/58, 62; 623/11; 29/407; 522/7

[56] References Cited

U.S. PATENT DOCUMENTS

| | | | |
|---|---|---|---|
| 4,380,855 | 4/1983 | Deckman et al. | 29/407 |
| 4,772,591 | 9/1988 | Meisner | 514/62 |
| 4,931,546 | 6/1990 | Tardy et al. | |
| 5,092,883 | 3/1992 | Eppley et al. | 623/11 |
| 5,264,207 | 11/1993 | Bommelaer et al. | 424/69 |
| 5,658,894 | 8/1997 | Weisz | 514/58 |
| 5,700,848 | 12/1997 | Soon-Shiong et al. | 522/7 |

OTHER PUBLICATIONS

Shlomo Margel, Reactive Polymers 1:241–250, 1983.
Horton, J.Cell Physiol 141: 8–15 (1989).
Grosschedl, Cell 38:647–658 (1984).
Swift, cell 38: 639–646 (1984).
Haukipuro, ann Surg 213:75–80 (1991).
Osborn, J. Orthop Res 7: 35–42 (1989).
McQuillan, Biochem J 240:423–430 (1986).
Ornitz, Cold Spring Harbor Symp 50: 399–409 (1986).
Rosen, J. cell Physiol 134: 337–346 (1988).
Alexander, Mol Cell Biol 7: 1436–1444 (1987).
Alexandrow, Cancer res 55: 1452–1457 (1995).
Shani, Nature 314: 283–286 (1985).
Adams, Nature 318: 533 (1985).
Selden, Science 236:714 (1987).
Momaerts, Proc Natl Acad Sci 88: 3084 (1991).
Mann, PNAS 92: 4502 (1995).
Hanahan, Nature 315: 115 (1985).
Mescher, J Immunol 149: 2402 (1992).
Thompson, Invest Radiol 26: 604 (1991).
Gentry, Mol cell Biol 7: 3418 (1987).

*Primary Examiner*—Marianne M. Cintins
*Assistant Examiner*—Vickie Kim
*Attorney, Agent, or Firm*—Graham & James LLP

[57] ABSTRACT

Therapeutic compositions of microspheres for application to wounds and/or lesions for accelerating wound healing and muscle regeneration. The microspheres are made up of non-biodegradable material having a substantial surface charge. The therapeutic composition further includes a pharmaceutically acceptable carrier in which the microspheres are insoluble and a container for holding the composition. The therapeutic composition further contains pharmacologic agents or biologics that accelerate the wound healing process.

31 Claims, 30 Drawing Sheets

EXPERIMENTAL RAT

HEALING OF WOUNDS, TREATED BY MICROSPHERES (CONTROL RAT) AND BY SALINE (CONTROL RAT) FIVE DAYS AFTER INJURY
FIG. 4C    CONTROL RAT
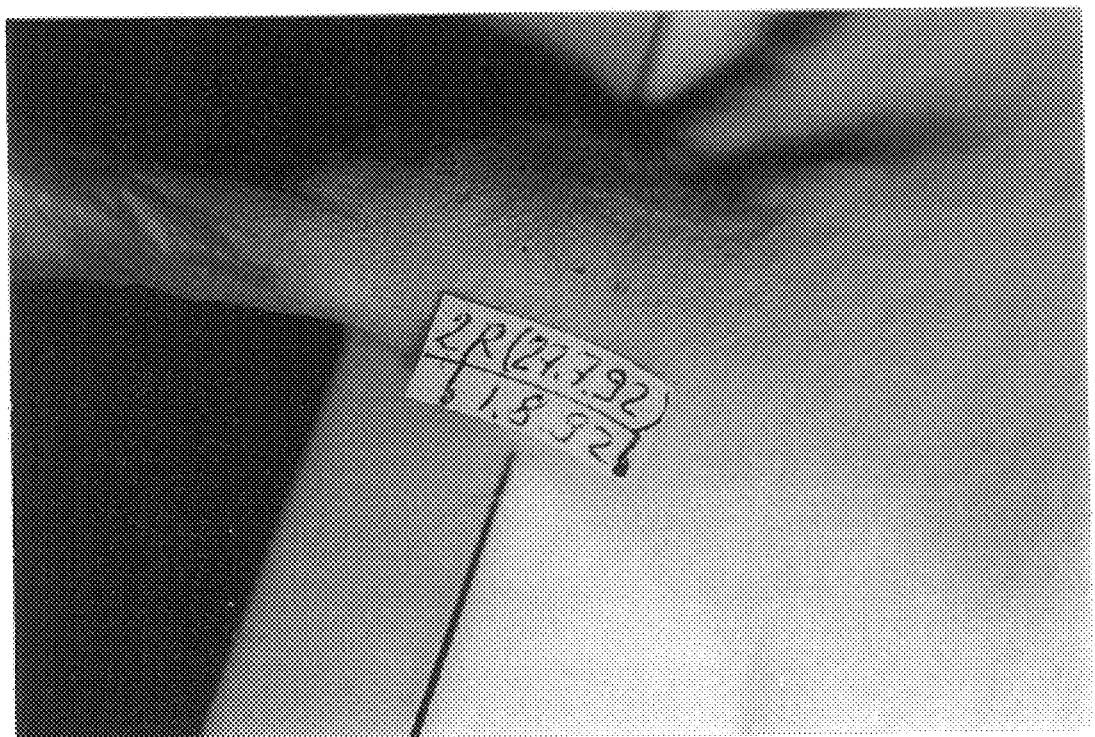
FIG. 4D    EXPERIMENTAL RAT

COMPOSITIONS OF MICROSPHERES FOR WOUND HEALING

The present application is a continuation-in-part of application Ser. No. 08/868,950, filed Jun. 4, 1997, now U.S. Pat. No. 5,861,149, which is incorporated by reference herein in its entirety.

1. FIELD OF INVENTION

The present invention relates to compositions of microspheres for application to wounds and/or lesions, and to methods of use of said composition alone or in combination with other agents in the prevention and treatment of wounds or lesions.

2. BACKGROUND OF THE INVENTION

Wound healing is a complex process involving such factors as cells, extracellular matrix components and the cellular microenvironment. Essentially, all wound healing involves the repair or replacement of damaged tissues including but not limited to skin, muscle, neurologic tissue, bone, soft tissue, internal organs or vascular tissue. The precise nature of such repair or replacement depends upon the tissues involved, although all such processes involve certain basic principles. An important aspect of wound healing is the rate at which a wound gains tensile strength.

Skin exhibits tension and extensibility. Skin tension is one of the determining factors in the response to a wound and varies with age and site. Skin has multiple layers, including keratin, epidermis and dermis and contains cells, a fibrous network composed of collagen and elastin and an amorphous ground substance which consists of protein polysaccharides, glycoproteins, globular proteins, salts and water. If only the epidermis is damaged, as in most minor injuries, keratinocytes migrate from the edge of the wound and eventually cover it, reforming the epidermis and keratin (Knighton, D. R. and Fiegel, V. D., 1991, Invest. Radiol: 26:604–611).

If all skin layers are damaged or destroyed, new connective tissue, called granulation tissue, must first fill the wound space. This tissue is formed by deposition of extracellular matrix components, for example, collagen, by fibroblasts which migrate into the wound space. The synthesis and deposition of collagen is an important event in wound healing and the rate of collagen synthesis varies in different organs (Haukipuro, K. et al., 1991, Ann. Surg. 213:75–80).

The entire multi-step process of wound healing must be completed for successful would healing. If one or more of these components is missing, healing does not take place, the skin is not repaired and the wound remains open. Such open wounds can easily become infected, further retarding the process of healing and leading to the formation of ulcers and sores on the skin. The process of wound healing is further inhibited in many patients by the presence of other complicating conditions, including, but not limited to diabetes or old age. Patients with such conditions often have skin wounds which ulcerate and refuse to heal, or only heal slowly after an extended period of time has elapsed.

Various treatments have been used in order to accelerate the rate at which wounds heal (U.S. Pat. No. 4,772,591; U.S. Pat. No. 4,590,212) and various pharmaceutical carriers have been employed to deliver chemotherapeutic agents to the wound, for example, creams, gels, powders and microspheres. U.S. Pat. No. 5,264,207 discloses microspheres of a polymer, which act as carriers for one or more active pharmaceutical or cosmetic substances. The polymer microspheres are solid or hollow, insoluble in the carrier liquid and are of varying dimensions, not exceeding 1000 nm (1 µm), with the preferred sizes ranging from 50 to 500 nm (0.05 µm to 0.5 µm) and the most preferred sizes ranging from 60 to 300 nm (0.06 µm to 0.3 µm). The fineness of the microspheres leads to higher specific area per unit weight and higher combination of microspheres to active substances without the disadvantage of conventional excipients which block skin pores. Thus, according to the invention of U.S. Pat. No. 5,264,207, a suspension of the microspheres can be obtained onto which an active substance is adsorbed, another substance binding to the microsphere by chemical bonds, with the possibility of a third substance binding to the microspheres by electrostatic or ionic bonds (Col. 2, lines 58–63). When the microspheres are hollow, they are both adsorbent and/or carriers of functional groups (Col. 3, lines 18–21). When the microspheres contain pores, bonding with a pharmaceutical or cosmetic substance consists of adsorption into the pores (Col. 3, lines 26–28). Thus, U.S. Pat. No. 5,264,207 discloses a composition of microspheres which act as carriers for pharmaceutical and/or cosmetic substances only and does not teach or suggest using only the microspheres themselves to enhance wound healing.

Similarly, PCT Application Nos. WO96/13164 and WO94/13333 both disclose microspheres made of a material which catalyzes the production or release of certain therapeutic substances. PCT Application No. WO96/13164 discloses polymeric nitric oxide adducts which release nitric oxide when directly applied to damaged tissue. PCT Application No. WO94/13333 discloses particles which are chemically modified to have free radical activity in the wound environment. Thus, neither reference teaches or suggests using the microspheres themselves as a therapeutic substance, without chemical modification of the microsphere material.

The size of the microspheres was shown to influence the effect of microspheres as carriers for the class I alloantigen used in the activation of cytotoxic T lymphocytes (Mescher, M. F., 1992, J. Immunol 149:2402–2405). The response was dependent on the class I antigen being presented on the optimum size of the microspheres of 4 or 5 µm diameter (4000 nm or 5000 nm). In other words, Mescher disclosed that the activation of T lymphocytes in vitro could not be achieved with microspheres alone but required the class I antigen to induce the activation. The antigen reacted optimally when bound to microspheres of 4 or 5 µm diameter, i.e. 4 to 5 times greater in size than microspheres used in U.S. Pat. No. 5,264,207, issued to Bommelser, J., et al. There is no teaching or suggestion in Mescher of using microspheres alone without the active component, class I antigen, in the activation of wound healing. In fact, the role of microspheres and cytotoxic T lymphocytes, in wound healing and collagen synthesis is not at all taught or suggested by Mescher. Furthermore, Bommelser teaches away from the use of microspheres greater than 1000 nm or 1 µm in size because larger microspheres would block skin pores. Thus, the present invention is neither inherent (because of the difference in the ingredients of the compositions of prior art) nor obvious (because the size of microspheres used would be expected from prior art to block skin pores) from the prior art.

The process of wound healing includes an initial proliferative phase promoting rapid cell metabolism and proliferation, disposal of debris, mobilization of fibroblasts and restoration of circulation. It is during this period that the wound is most susceptible to infection. During the subsequent phase (also referred to as the fibroplastic phase) of wound healing, increasing tensile strength parallels the rise in collagen content of the wound. Thus, there has remained a need to develop compositions for wound healing such that they contain non-biodegradable microspheres and other extracellular components capable of promoting the proliferative phase and regulating the fibroplastic phase in situ.

Hence, there must be a balance between promotion of the proliferative phase and the onset of the fibroplastic phase during wound healing in animals and human beings for different conditions including, but not limited to, burned tissues, infections following surgery, surgery wound breakdown, internal ulcers, hemorrhage, bone gangrene, pressure sores, decubitis, compromised amputation sites, non-healing traumatic wounds, cosmetics, after shave, dental work, chronic ulcers (of the diabetics, varicose vein, post stroke), destruction of tissue by radiation, spinal injury wounds, gynecological wounds, chemical wounds, vessel disease wounds, diabetic skin sores, diabetic feet, physical trauma, post plastic surgery suture sites, sunburns or episiotomies.

3. SUMMARY OF THE INVENTION

It is therefore an object of the present invention to produce a prophylactic and therapeutic compositions that can prevent wound formation or promote wound healing and that can function as a wound/lesion dressing when applied to the contours of and within the wound or lesion.

It is another object of the present invention to provide a composition that can function as a wound dressing that will serve as a promoter of regeneration of muscle, skin, cartilage, neurologic tissue, soft tissue or vascular tissue.

It is yet another object of the present invention to provide a composition that can function as a wound/lesion covering that is, when wet, adherent and will remain in contact with the wound/lesion site without the need of a potentially toxic adhesive.

It is yet another object of the present invention to provide a composition that can serve as a medium for microspheres and a drug delivery system for pharmaceutical agents.

It is yet another object of the present invention to provide a composition that will serve to promote myoblast fusion.

It is another object of the present invention to provide a composition that will serve to promote collagen synthesis in vitro and in vivo.

It is yet another object of the present invention to provide a composition that will prevent scar formation.

It is another object of the present invention to provide a composition including microspheres and exogenous growth factors added to it that will serve to promote wound healing.

It is yet another object of the present invention to provide a composition including microspheres and anti-inflammatory agents.

It is yet another object of the present invention to provide a composition including microspheres and antihistaminic agents.

It is yet another object of the present invention to provide a composition including microspheres and antibiotics.

It is yet another object of the present invention to provide a composition including microspheres and vitamins.

It is yet another object of the present invention to provide a composition including microspheres and minerals.

It is yet another object of the present invention to provide a composition including microspheres and anticancer agents, antiviral agents and antifungal agents.

It is yet another object of the present invention to provide a composition including microspheres with or without an active substance, that is applied as adjuvant therapy to surgery, radiation therapy, hormone therapy or chemotherapy.

It is yet another object of the present invention to provide a composition including microspheres and an analgesic, anesthetic or astringent.

It is yet another object of the present invention to provide a composition including microspheres and collagen.

It is yet another object of the present invention to provide a composition including microspheres and one or more of the agents selected from the group consisting of anti-inflammatory antihistaminic, antibiotic, antiseptic, antifungal, analgesic, anesthetic, minerals, vitamins, astringent agent and collagen.

It is yet another object of the present invention to provide a composition including microspheres and stromal cells that will serve to promote wound healing.

It is yet another object of the present invention to provide a composition including microspheres and genetically engineered stromal cells which express a gene product beneficial for successful and/or improved wound healing. For example, in the case of diabetic sores, the fibroblasts can be genetically engineered to express insulin growth factor (IGF) or anticoagulation gene products to reduce the risk of atherosclerosis, occlusion, or anti-inflammatory gene products to reduce the risk of failure to heal. Alila, H. et al., 1997, Human gene Ther. 8:1785–1795; and Pickering, J. G. et al., 1996, Semin. Interv. Cardiol. 1;84–88.

In accordance with the present invention, the composition comprises microspheres having charged surface groups, wherein the charge can be negative or positive. The microsphere material is selected from the group consisting of polystyrene, derivatized polystyrene, polymethylmethacrylate (PMMA), silicone, polylysine, poly-N-ethyl-4-vinylpyridinium bromide and latex. According to certain embodiments of the present invention, the charged surface groups are selected from the charged groups consisting of polystyrene, derivatized polystyrene, sulfate, poly-N-ethyl-4-vinylpyridinium bromide, protamine, protamine sulfate, protamine salts, polylysine and carboxyl. Also preferably, the microsphere has a diameter in a range of from about 0.01 microns to about 200 microns, more preferably in a range of from about 1 to about 100 microns, and most preferably from about 2 to about 20 microns. According to another embodiment of the present invention, the composition also includes a pharmaceutically acceptable carrier for the microsphere.

In accordance with the present invention, the composition includes a pharmaceutically acceptable carrier suitable for forming a gel preparation, including but not limited to methyl cellulose, agarose, dextrans, polysaccharides, gelatine, aloe vera extract (Acemanman-beta-(1,4)-linked acetylated mannan or other pharmaceutically acceptable vehicles.

In accordance with the present invention the composition includes a pharmaceutically acceptable carrier suitable for forming a liquid preparation, comprising a tissue culture medium (e.g., Dulbecco's Modified Eagle Medium), saline, or other pharmaceutically acceptable vehicles.

In accordance with the present invention, the composition for treating a wound includes microspheres capable of forming a multipoint contact with a cellular membrane and a pharmaceutically acceptable carrier in which the microspheres are substantially insoluble, and a container for holding the composition. As exemplified, the carrier is preferably selected from the group consisting of aqueous medium, aerosol carrier, ointment and bandage.

In accordance with the present invention, there is provided a composition for promoting muscle regeneration, including microspheres capable of forming multi-point contacts with cellular membrane and a pharmaceutically acceptable carrier in which the agent is substantially insoluble.

In accordance with the present invention, there is provided a container holding a composition of microspheres in aseptic condition and capable of forming multi-point contacts with cellular membrane.

In accordance with the present invention, there is provided a container holding an aseptic composition of microspheres and one or more active substances.

In accordance with the present invention, there is provided a container holding an aseptic composition of microspheres and one or more further containers, each holding a preparation of an active substance, which can be mixed with the microspheres prior to application to the wound, or which can be applied separately to the wound site.

4. BRIEF DESCRIPTION OF THE FIGURES

For a more complete understanding of the present invention, and the advantages thereof, reference is now made to the following descriptions taken in conjunction with the accompanying drawings, in which:

FIGS. 4A–4D illustrate the ability of the microspheres to promote wound healing in rats;

Figure 6A:
Figure 6B:
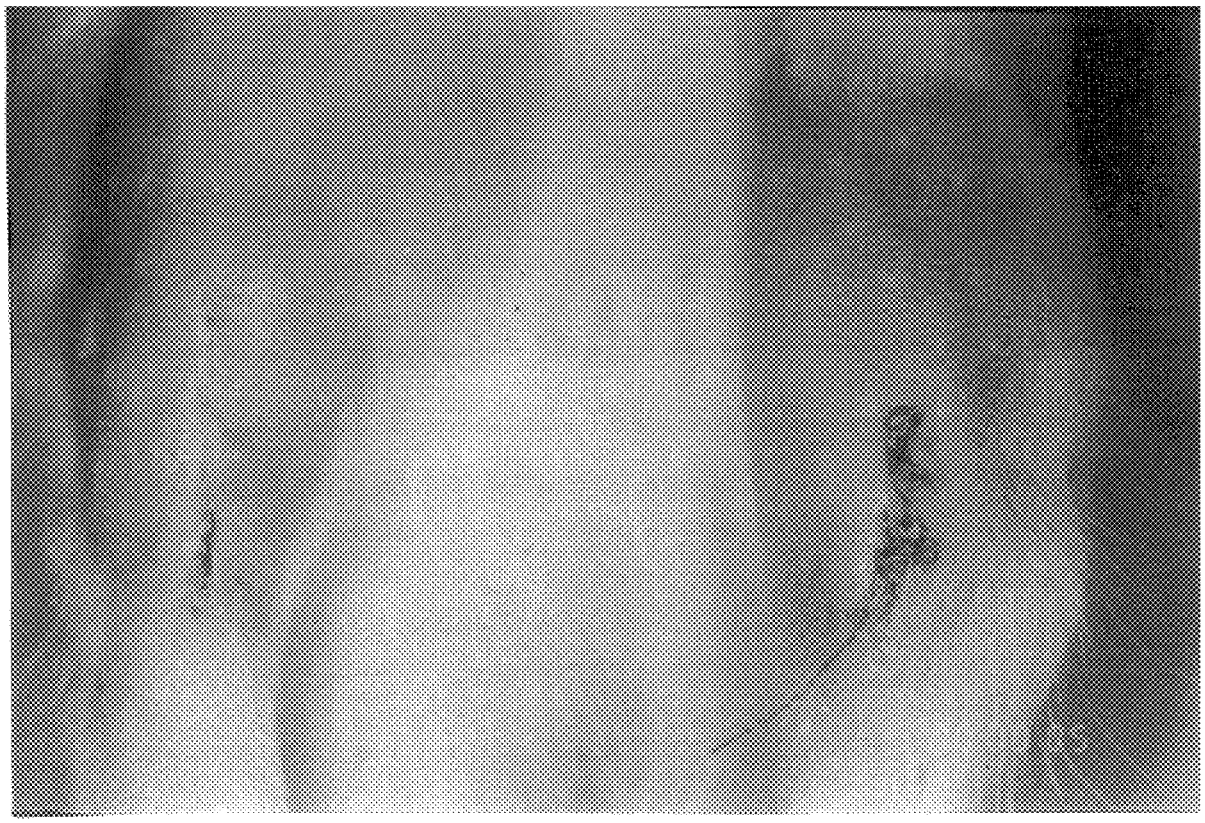
Figure 7A:
Figure 7B:
Figure 7C:
Figure 7D:
Figure 8A:
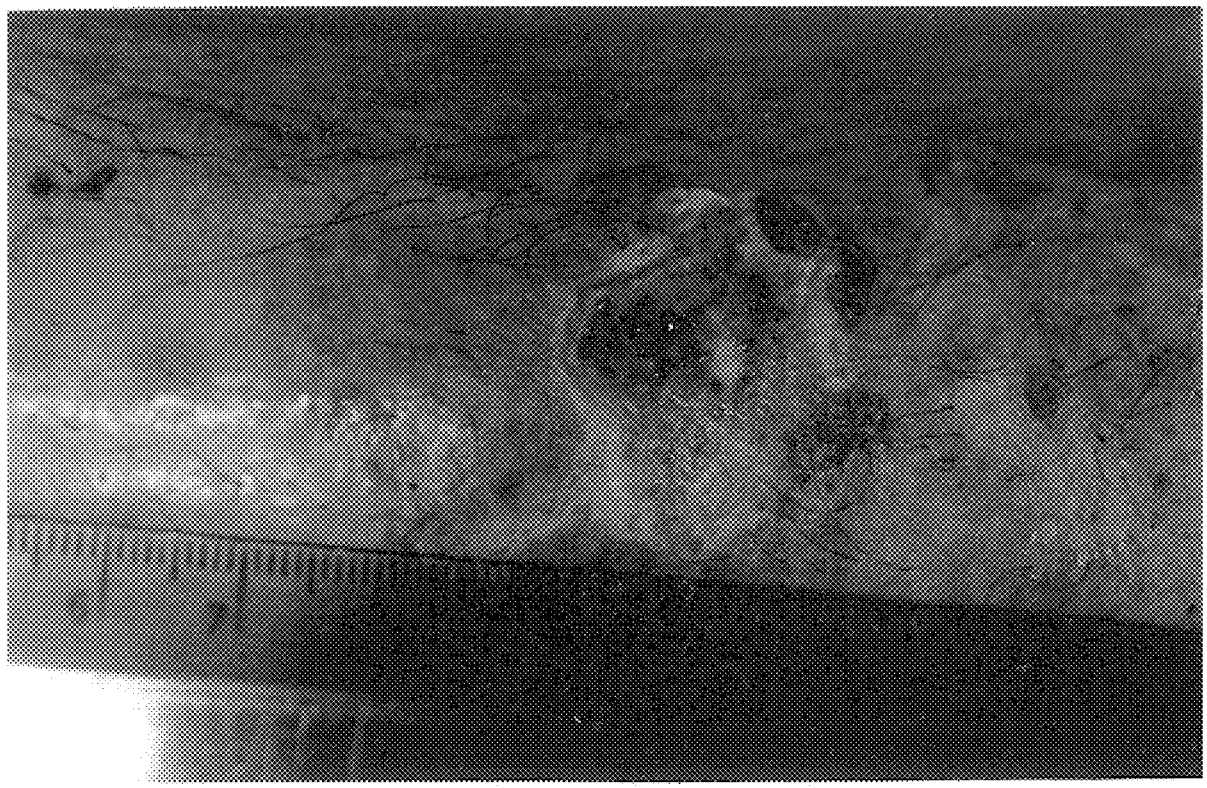
Figure 8B:
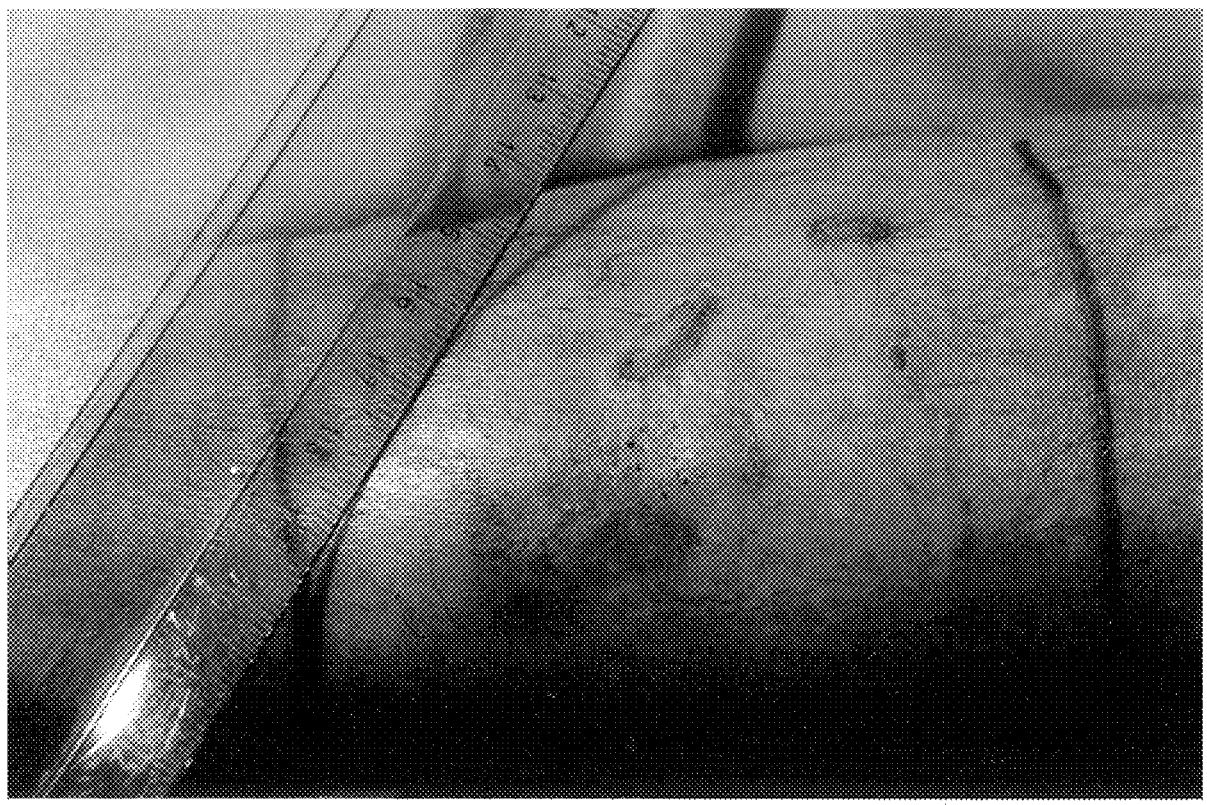
Figure 9A:
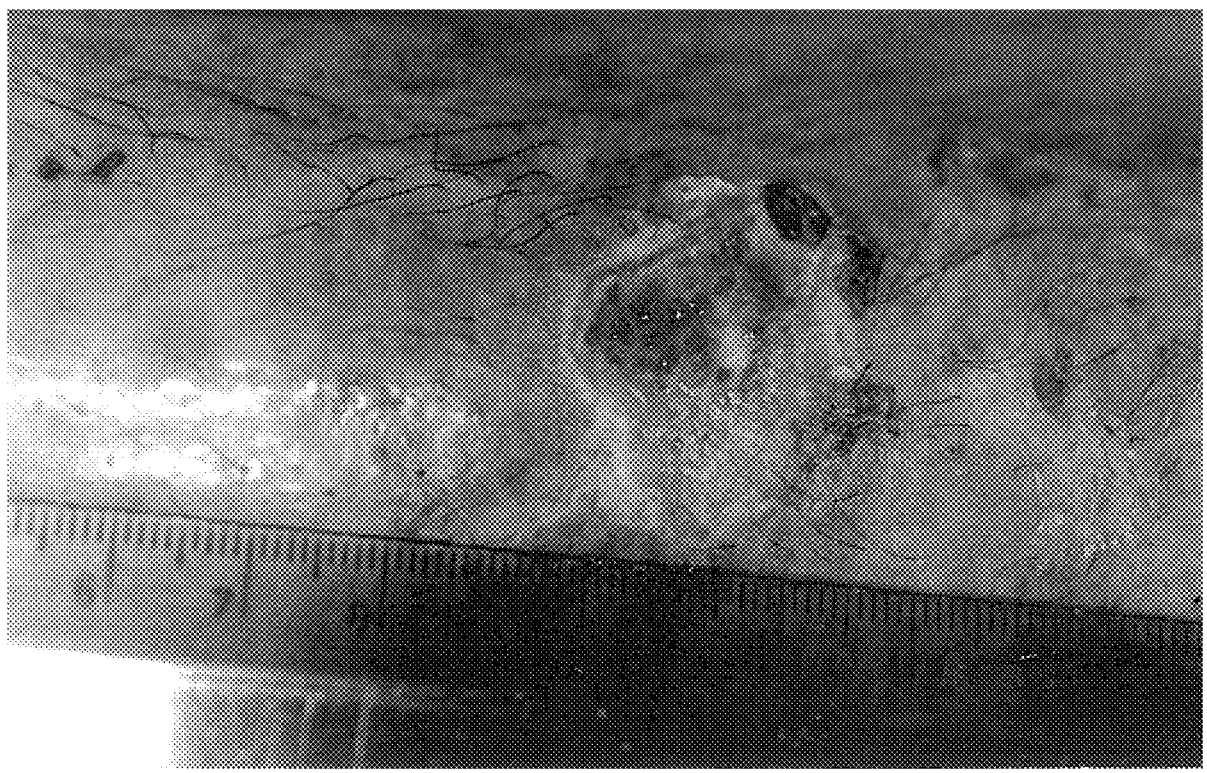
Figure 9B:
Figure 10A:
Figure 10B:
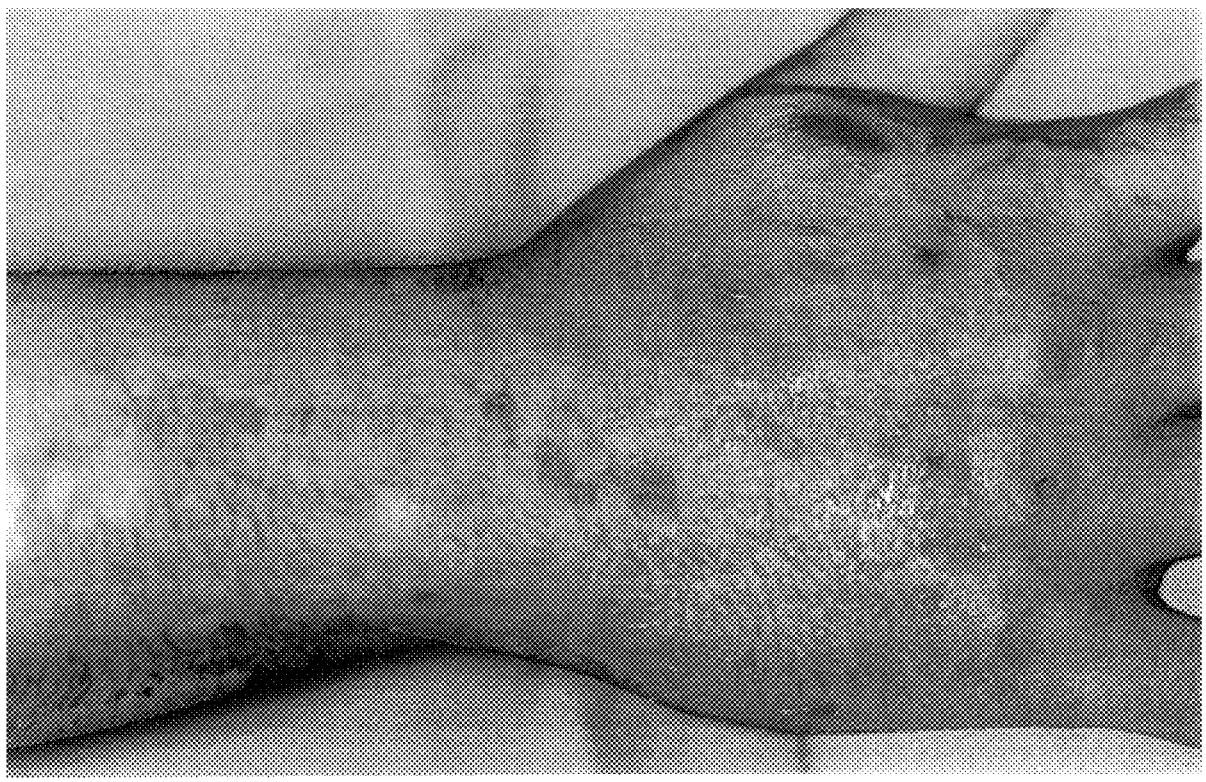
Figure 10C:
Figure 10D:
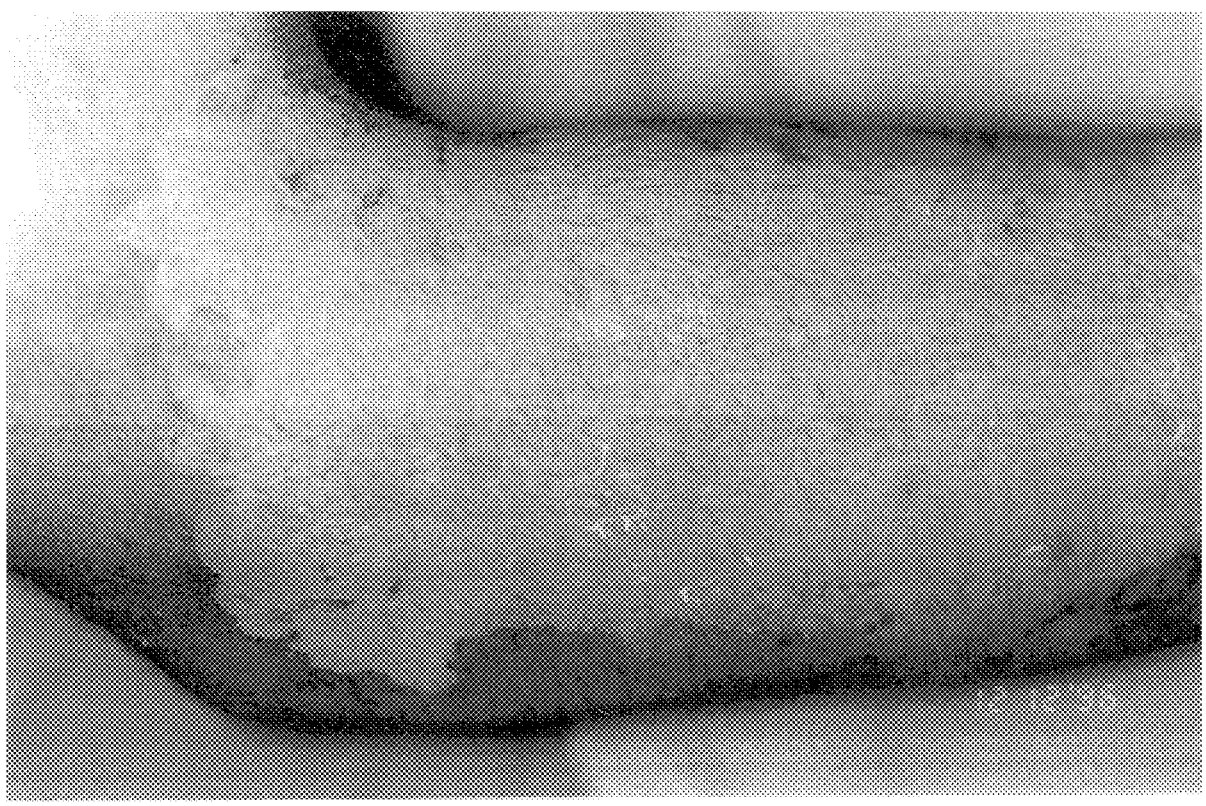
Figure 11A:
Figure 11B:
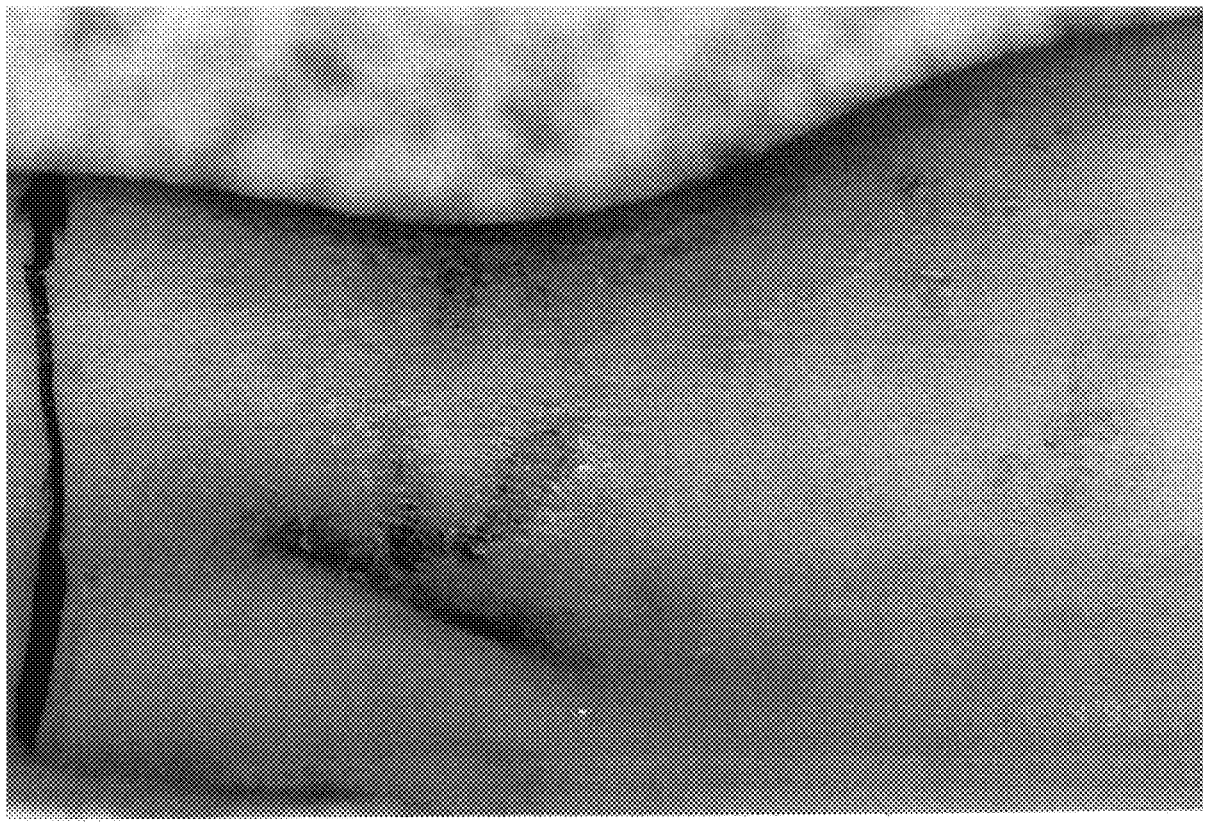

FIGS. 6A and 6B compare the effect of the microspheres of the present invention on wound healing with tissue culture media and saline in rats;

FIGS. 7A–7D demonstrate the ability of the microspheres of the present invention to promote wound healing in a first human case study;

FIGS. 8A and 8B further demonstrate the efficacy of the present invention in the human case study of FIGS. 7A–7D;

FIGS. 9A and 9B demonstrate the efficacy of the present invention in a second human case study;

FIGS. 10A–10D show the effect of the present invention in a third human case study; and FIGS. 11A and 11B show the efficacy of the present invention in a fourth human case study.

FIGS. 12A–12D describe the effect of the present invention in an individual when given in combination with radiation therapy and chemotherapy.

5. DETAILED DESCRIPTION OF THE INVENTION

The present invention relates to prophylactic and therapeutic compositions and a method for promoting wound healing by using microspheres. Unexpectedly, microspheres of the particular size range described herein are able to promote wound healing without the further addition or inclusion of any drug or other therapeutic substance. Indeed, as described below, these microspheres do not degrade or undergo other chemical alteration in order to produce their therapeutic effect. The microspheres of the present invention can also be administered as adjuvant therapy to conventional therapies, e.g., radiation, chemotherapy, hormone, laser, high pressure or ozone therapy.

5.1 Characteristics of Microspheres

The structure of these microspheres includes a core material and at least one type of charged surface group which is present at least on the exterior of the microsphere. Examples of materials include long-chain polymers such as polystyrene, latex, poly-β-alanine, polymethylmethacrylate (PMMA), silicone and derivatized polystyrene. Examples of surface groups include sulfate, poly-N-ethyl-4-vinylpyridinium bromide, protamine, protamine sulfate, protamine salts, polylysine, carboxyl and polystyrene. These surface groups may be present as part of the core material, or may be added later by such chemical processes as derivatization of the long-chain polymer. Hereinafter the term "derivatization" refers to the process of chemically altering, modifying or changing a molecule or a portion thereof. The microspheres produced from the polymer should be substantially insoluble in aqueous media, instead forming a suspension or dispersion in such media.

In order to further clarify the parameters of the present invention, a number of terms should be defined. Hereinafter, the terms "wound" or "lesion" includes any injury to any portion of the body of a subject including, but not limited to, acute conditions such as thermal burns, chemical burns, radiation burns, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, those injuries sustained in automobile and other mechanical accidents, and those caused by bullets, knives and other weapons, and post-surgical injuries, as well as chronic conditions such as pressure sores, bedsores, conditions related to diabetes and poor circulation, and all types of acne. Areas of the body which can be treated with the present invention include, but are not limited to, skin, muscle, neurologic tissue, bone, soft tissue, vascular tissue, and internal organs. Hereinafter, the term "subject" refers to a human mammal or lower animal on whom the present invention is practiced.

Hereinafter, the term "promoting" includes accelerating and enhancing. Hereinafter, "reducing scarring" includes preventing or decreasing excess scar formation such as keloids and hypertrophic scars, as well as decreasing the extent of scar tissue formation both externally such as on the skin of the subject, and internally such as adhesions. Finally, it should be noted that the method of the present invention may also be used cosmetically, to prevent excess scar formation in a cut or other wound to the skin such as the skin of the face, and to treat acne. In a cosmetic sense, the term "excess scar formation" includes any scarring which is cosmetically undesirable or unacceptable.

Although the discussion below refers to specific types of microspheres, it should be noted that this is not intended to be limiting in any way. It will be appreciated to those skilled in the art that these microspheres, more generally, can be beads, particles or globules which are either solid or hollow. In preferred embodiments of the present invention, these microspheres are dispersed in a pharmaceutically acceptable carrier medium in which the agents are substantially insoluble, as a suspension in aqueous medium for example, or in a non-aqueous medium such as an ointment, aerosol spray, or a bandage which may be occlusive or non-occlusive. The shape of the microspheres can be regular, such as spherical or elliptical, or regular non-spherical shapes; or the shape of the particles can be non-regular, so that the surface is not a single continuous curve or so that the surface is not smooth.

Furthermore, the microspheres can be a mixture of different polymers and can also be a mixture of different particles, beads or globules of different sizes. The agents can also have pores of different sizes.

By way of example, the long-chain polymer forming the agents, such as poly-β-alanine, can be cross-linked, which particularly favors the spherical shape of a microsphere, although such a shape can be obtained without cross-linking. An example of a method of manufacture for a cross-linked poly-β-alanine microsphere is given in U.S. Pat. No. 5,077,058, although it should be noted that this material would require further derivatization to obtain an overall surface charge of the microsphere.

Alternatively, the particles can have chaotic irregular forms, particularly if the polymer is not cross-linked. The particle can have any form, such as coiled, globular, extended and random coil. Preferably, the polymer should not be biochemically reactive and should be non-biodegradable. Most preferably, the polymer is non-biodegradable substantially during the treatment period, so that it would remain undegraded during the period required for healing of the wound. Hereinafter, the term "non-biodegradable" refers to agents which are not biodegradable during the treatment period, which is the period required for treatment of the wound.

At the very least, the agents should have the following properties:

1. They should be capable of forming multi-point contacts with cells or portions of cells thereof, such as the outer cell membrane and molecules on this membrane;
2. They should be able to promote wound healing without significant chemical alteration or degradation; and
3. They should be substantially insoluble in aqueous media such as bodily fluids, and instead should form a suspension.

These characteristics are important because as further discussed below, the effect of the agents of the present invention appears to be directly related to the formation of multi-point contacts between the material of the agents and a portion of the cell such as the outer cell membrane, thereby forming an adherent surface for the cells to attach to. Such multi-point contacts are possible with many different polymers which permit charged groups to be accessible for interaction with molecules and portions of the outer cell membrane. Thus, although the description below focuses on one type of agent, microspheres, it is understood that the present invention covers any material capable of forming such multi-point contacts.

As noted above, preferably the microsphere has a diameter in a range of from about 0.01 microns to about 200 microns, more preferably in a range of from about 1 to about 100 microns, and most preferably from about 2 to about 20 microns. The microsphere composition of the present invention comprises 0.001 to 25 percent by weight in suspension. Without desiring to be bound by any mechanism, it should be noted that these preferred ranges are the best size for enabling uptake of the microspheres by macrophages infiltrating the wound area. The microspheres appear to actually attract and activate the macrophages through contact with at least a portion of the macrophages, probably the molecules of the outer cell membrane of the macrophage. The anti-inflammatory and anti-bacterial effects observed for the microspheres are thus presumably indirect effects, obtained through the activation of the macrophages or other cells.

Another important property of the microspheres is the charge of the surface groups. The overall charge carried by certain preferred examples of microspheres was measured as a Z or zeta potential by electrophoretic mobility (millivolts) by a ZetaMaster (Malvern Instruments, United Kingdom). The range of Z potentials measured in certain embodiments exemplified herein was from −29.58 mV to −79.7 6 mV. Hereinafter, the term "charged" refers to a Z potential with an absolute value of at least about 1 mV, and preferably of at least about 10 mV, whether negative or positive.

The microspheres in the suspensions tested did not aggregate, coalesce, clump or undergo irreversible caking. Although the microspheres did settle somewhat over time, they were easily resuspended with gentle agitation.

The microspheres of the present invention are akin to a liquid bandage or device that can be applied on the contours of a wound or within the wound. The microsphere s are packaged in a sterile container under argon, neon or nitrogen at an optimum pH and varying concentration and volume by conventional methods.

5.2 Pharmacological and Biologic Agents

Any one or more of the following kinds of pharmacological agents can be included in the prophylactic or therapeutic compositions along with the untreated microspheres: antiseptics, astringents, antifungal agents, antiviral agents, anticancer agents, antihistamines, antibiotics, blood coagulants for battlefield use, vitamin and mineral preparations, vitamins, minerals or anti-inflammatory agents.

Biologically active substances which can be included in the therapeutic composition include, but are not limited to astringents, antibiotics, oxidants, proteolytic enzymes, collagen cross-link inhibitors (e.g. natural or synthetic diamines-cystamine, putrescine, spermidine, cadaverine and the like), amino acids, macrophage stimulating factors, or anesthetics.

Growth and regulatory factors may be added to the therapeutic composition to enhance the wound healing process by aiding in the formation of granulation tissue and re-epithelization, for example, but not limited to platelet-derived growth factor (PDGF), platelet-derived angiogenesis factor (PDAF), platelet-derived epidermal growth factor (PDEGF), transforming growth factor-beta (TGFB), platelet factor (PF-4), alpha and beta fibroblast growth factors (αFGF and βFGF) growth hormone (GH), epidermal growth factor (EGF) or insulin growth factor (IGF).

Platelet-derived growth factors stimulate the cascade systems involved in wound healing especially during the phases of granulation formation and re-epithelization. Transforming growth factor-beta refers to a growing family of related dimeric proteins which regulate the proliferation and differentiation of many cell types (Massague, 1990, Ann. Rev. Cell. Biol. 6:597–619). TGFB also induces the production of cartilage-specific macromolecules in muscle cells and chondrocytes. However, TGFB was found to inhibit the synthesis of collagen type II by chicken sternal chondrocytes (Horton et al., 1989, J. Cell Physiol. 141:8–15) and by rat chondrocytes (Rosen et al., 1988, J. Cell Physiol. 134:337–346).

In fact, TGFB has emerged as a prototypical inhibitor of the proliferation of most normal cell types in vitro and in vivo (Alexandrow, A. G., et al., 1995, Cancer Res. 55: 1452–1457). $TGFB_1$ has been purified from human and porcine blood platelets and recombinant $TGFB_1$ is currently available (Gentry et al., 1988, Mol. Cell. Biol.

7:3418–3427). Insulin alone is much less potent than IGF-I in stimulating collagen matrix synthesis. IGF-II stimulates DNA and RNA synthesis and is more potent than IGF-I in stimulating clonal growth in fetal cells (McQuillan, et al., 1986, Biochem. J. 240:423–430). Epidermal growth factor alone has no effect on chondrocyte proliferation. Together with insulin, EGF synergistically stimulates proliferation of chondrocytes (Osborn, K. D., et al., 1989, J. Orthop. Res. 7:35–42).

High levels of lipid peroxides have been demonstrated in activated macrophages, aggregated platelets, and subcellular particles isolated from injured tissue. Strong oxidants, drugs metabolized to free radicals, and ionizing radiation all induce prostaglandins, leukotrienes (eicosanoids) and/or lipid peroxidative increases. These increased eicosanoids and lipid peroxides may be one cause of tissue damage or necrosis and of the increase in the inflammatory reaction. The inclusion of anti-inflammatory drugs, e.g. non-steroidal anti-inflammatory drugs (ibuprofen, indomethacin, aspirin, acetaminophen, naproxen, sulindac) and specifically the cyclooxygenase-2 (COX2) inhibitors, in the prophylactic and/or therapeutic composition may prove useful in all injured tissues, for example, in lung, liver, radiation-induced injury in which fibrosis is a prominent consequence of prolonged or repeated injury. In addition, the inclusion of anti-oxidants (e.g., vitamin E) and free radical scavengers (e.g., reduced glutathione) may also prove useful.

Zinc—It has been demonstrated that after trauma, surgical or otherwise, the amount of zinc in blood and tissues may fall to low levels. This is particularly noticeable in burned patients. Administration of zinc sufficient to restore normal levels of this trace element in blood and tissues increases rate of epithelization, rate of gain of wound strength, and synthesis of collagen and other proteins. A number of enzymes are zinc-dependent notably DNA-polymerase and reverse-transcriptase. The effects of zinc depletion on wound healing are what one would expect if the amount of functions of these enzymes were depressed. Epithelial and fibroblast proliferation does not occur, since mitosis of these cells cannot take place without DNA polymerase and reverse-transcriptase. Thus, although these cells may migrate normally, they do not multiply; hence adequate epithelization does not occur and collagen synthesis by the few fibroblasts migrating into the wound cannot supply the fibers needed to hold the wound together. In such a case raising blood and tissue zinc concentrations to normal will restore normal progression of wound healing. It is the object of the present invention that in patients in whom blood and tissue zinc levels are low, administration of zinc orally, parenterally or topically in the therapeutic composition will restore normal wound healing. Zinc will be provided as a salt selected from the group consisting of zinc chloride, zinc carbonate and/or zinc gluconate.

Vitamin A and E

Vitamin A can partially reverse the retarded development of granulation tissue and reduced amounts of collagen in wound healing. Vitamin A applied topically enhances epithelization in wounds retarded by corticosteroid administration, but collagen deposition is affected by systemic vitamin A only.

Vitamin E can be used to modify scar formation since its side effects are less than those of comparable amounts of steroid hormones. In high doses, vitamin E retards wound healing and collagen production but this effect is overcome in the presence of vitamin A. It is therefore, another objective of the present invention to provide vitamins A and E to subject in need thereof, orally, parenterally or topically in the prophylactic and/or therapeutic composition of the present invention.

5.3 Gene Therapy

The prophylactic and/or therapeutic composition of the present invention may afford a vehicle for introducing genes and gene products in vivo to accelerate the wound healing process. For example, for diabetic sores, the therapeutic composition includes the microspheres of the present invention and genetically engineered stromal cells (e.g. fibroblasts with or without other cells and/or elements found in loose connective tissue taken from the subject, including but not limited to, endothelial cells, pericytes, macrophages, monocytes, plasma cells, mast cells, adipocytes, etc.) which use genetically engineered to express anticoagulation gene products to reduce the risk of thromoembolisim, or anti-inflammatory gene products to reduce the risk of failure due to inflammatory reactions. Once genetically engineered cells are applied into the wound site, the presence of the anti-inflammatory gene products, for example, peptides or polypeptides corresponding to the idiotype of neutralizing antibodies for tumor necrosis factor (TNF), interleukin-2 (IL-2) or other inflammatory cytokines, can bring about amelioration of the inflammatory reactions associated with diseases including but not limited to burned tissues, infections following surgery, diabetic neuropathic ulcers, pressure ulcers, venous stasis ulcers, burned tissues, infections following surgery, surgery wound breakdown, internal ulcers, hemorrhage, bone gangrene, pressure sores, decubitis, compromised amputation sites, non-healing traumatic wounds, cosmetics, after shave, dental work, chronic ulcers (of the diabetics, varicose vein, post stroke), destruction of tissue by radiation, spinal injury wounds, gynecological wounds, chemical wounds, vessel disease wounds, diabetic skin sores, diabetic feet, physical trauma, post plastic surgery suture sites, sunburns or episiotomies.

Preferably, the cells are engineered to express such gene products transiently and/or under inducible control during the initial phase of wound healing, or as a chimeric fusion protein anchored to the stromal cells, for example, a chimeric molecule composed of an intracellular and/or transmembrane domain of a receptor or receptor-like molecule, fused to the gene product as the extracellular domain. In another embodiment, the stromal cells could be genetically engineered to express a gene for which a patient is deficient, or which would exert a therapeutic effect, e.g. HDL, apolipoprotein E, etc. The genes of interest engineered into the stromal cells need to be related to the disease being treated.

The stromal cells can be engineered using a recombinant DNA construct containing the gene used to transform or transfect a host cell which is cloned and then clonally expanded in the culture system. The culture which expresses the active gene product, could be implanted into an individual who is deficient for that product. For example, genes that prevent or ameliorate symptoms of various types of vascular, may be underexpressed or down regulated under disease conditions. Specifically, expression of genes involved in preventing the following pathological conditions may be down-regulated, for example: thrombus formation, inflammatory reactions, and fibrosis and calcification of the valves. Thus, the level of gene activity may be increased by either increasing the level of gene product present or by increasing the level of the active gene product which is present in the three-dimensional microsphere culture system.

Further, patients may be treated by gene replacement therapy during the fibroplastic phase of wound healing. Stromal cells may be designed specifically to meet the requirements of an individual patient, for example, the stromal cells may be genetically engineered to regulate one or more genes; or the regulation of gene expression may be transient or long-term; or the gene activity may be non-inducible or inducible. For example, one or more copies of a normal target gene, or a portion of the gene that directs the production of a normal target gene protein product with target gene function, may be inserted into human cells that populate the three-dimensional constructs using either non-inducible vectors including, but are not limited to, adenovirus, adeno-associated virus, and retrovirus vectors, or inducible promoters, including metallothionein, or heat shock protein, in addition to other particles that introduce DNA into cells, such as liposomes or direct DNA injection or in gold particles.

The use of the stromal cell in the therapeutic composition in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the three-dimensional cultures of the invention allow for expansion of the number of transfected cells and amplification (via cell division) of transfected cells.

A variety of methods may be used to obtain the constitutive or transient expression of gene products engineered into the stromal cells. For example, the transkaryotic implantation technique described by Seldon, R. F., et al., 1987, Science 236:714–718 can be used. "Transkaryotic", as used herein, suggests that the nuclei of the implanted cells have been altered by the addition of DNA sequences by stable or transient transfection. The cells can be engineered using any of the variety of vectors including, but not limited to, integrating viral vectors, e.g. retrovirus vector or adeno-associated viral vectors, or non-integrating replicating vectors, e g. papilloma virus vectors, SV40 vectors, adenoviral vectors; or replication-defective viral vectors. Where transient expression is desired, non-integrating vectors and replication defective vectors may be preferred, since either inducible or constitutive promoters can be used in these systems to control expression of the gene of interest. Alternatively, integrating vectors can be used to obtain transient expression, provided the gene of interest is controlled by an inducible promoter.

Any promoter may be used to drive the expression of the inserted gene. For example, viral promoters include but are not limited to the CMV promoter/enhancer, SV40, papillomavirus, Epstein-Barr virus, elastin gene promoter and b-globulin. If transient expression is desired, such constitutive promoters are preferably used in a non-integrating and/or replication-defective vector. Alternatively, inducible promoters could be used to drive the expression of the inserted gene when necessary. For example, inducible promoters include, but are not limited to, metallothionein and heat shock protein.

Examples of transcriptional control regions that exhibit tissue specificity for connective tissues which have been described and could be used, include but are not limited to: elastin or elastase I gene control region which is active in pancreatic acinar cells (Swit et al 1984, Cell 38:639–646; Ornitz et al. 1986, Cold Spring Harbor Symp. Quant. Biol. 50:399–409; MacDonald, 1987, Hepatology 7:425–515). The deposition of elastin is correlated with specific physiological and developmental events in different tissues, including the vascular grafts. For example, in developing arteries, elastin deposition appears to be coordinated with changes in arterial pressure and mechanical activity. The transduction mechanisms that link mechanical activity to elastin expression involve cell-surface receptors. Once elastin-synthesizing cells are attached to elastin through cell-surface receptors, the synthesis of additional elastin and other matrix proteins may be influenced by exposure to stress or mechanical forces in the tissue (for example, the constant movement of the construct in the bioreactor) or other factors that influence cellular shape.

The stromal cells used in the microsphere culture system of the invention may be genetically engineered to "knock out" expression of factors or surface antigens that promote clotting or rejection at the implant site. Negative modulatory techniques for the reduction of target gene expression levels or target gene product activity levels are discussed below. "Negative modulation", as used herein, refers to a reduction in the level and/or activity of target gene product relative to the level and/or activity of the target gene product in the absence of the modulatory treatment. The expression of a gene native to stromal cell can be reduced or knocked out using a number of techniques, for example, expression may be inhibited by inactivating the gene completely (commonly termed "knockout") using the homologous recombination technique. Usually, an exon encoding an important region of the protein (or an exon 51 to that region) is interrupted by a positive selectable marker (for example neo), preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted. Mombaerts, P., 1991, Proc. Nat. Acad. Sci. U.S.A. 88:3084–3087.

Antisense and ribozyme molecules which inhibit expression of the target gene can also be used in accordance with the invention to reduce the level of target gene activity. For example, antisense RNA molecules which inhibit the expression of major histocompatibility gene complexes (HLA) shown to be most versatile with respect to immune responses. Still further, triple helix molecules can be utilized in reducing the level of target gene activity. These techniques are described in detail by L. G. Davis, et al., eds, Basic Methods in Molecular Biology, 2nd ed., Appleton & Lange, Norwalk, Conn. 1994.

In another alternative, the stromal cells can be genetically engineered to block gene expression necessary for the transition of smooth muscle cells to proliferate, migrate and to lead to development of neointimal hyperplasia, e.g., by antisense oligodeoxynucleotide blockade of expression of cell division cycle 2 kinase and proliferating cell nuclear antigen. Mann, M. J., et al., 1995, Proc. Natl. Acad. Sci. USA 92:4502–4506.

The use of the stromal cell culture in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the stromal cell cultures of the invention allow for expansion of the number of transfected cells and amplification (via cell division) of transfected cells. For example, genetically engineered cells that express wound healing factors may be incorporated into the living stromal cultures used to make tendons and ligaments to enhance wound healing at the site of injury.

Examples of transcriptional control regions that exhibit tissue specificity which have been described and could be used, include but are not limited to: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald,1987, Hepatology 7:42S-S5S); insulin gene control region which is active in pancreatic beta cells (Hanahan, 1985, Nature 315:115–122); immunoglobulin gene control region which is active in lymphoid cells (Grosschedl et al.,1984, Cell 38:647–658;.Adams et al., 1985, Nature 318:533–538; Alexander et al., 1987, Mol. Cell. Biol. 7:1436–1444); and myosin light chain-2 gene control region which is active in skeletal muscle (Shani, 1985, Nature 314:283–286).

5.4 Wounds/Lesions (A) The Diabetic Foot

From 50–70% of all nontraumatic amputations in the United States is in the diabetics (A Report of the National Diabetes Board:NIH Publication 81-2284, 1980, p25). The breakdown of the foot in the diabetic is commonly due to a combination of neuropathy and infection, with or without some vascular impairment. If an ingrown toenail or ulcer occurs and remains untreated because of lack of pain sensation, the infection may spread throughout the foot, creating a gross infection that demands more blood supply than the impaired vessels can provide. The resulting gangrene may demand an amputation. Physicians sometimes get the impression that trophic ulcers in diabetics occur without loss of sensation. They are then surprised when breakdown occurs. The problem is that a foot may be vulnerable to damage long before gross sensory loss is noted. The therapeutic compositions of the present invention are designed to prevent the breakdown and to treat the ulcers associated with diabetics.

(B) Pressure Ulcers

Pressure ulcers continue to be a major healthcare problem especially for the elderly patient with limited mobility. The risk of death among geriatric patients increases fourfold when a pressure ulcer develops and sixfold when a ulcer does not heal. Development of pressure ulcers has been recognized as a source of malpractice liability for all who provide patient care. Courts have shown little sympathy for healthcare providers who permit such wounds to occur or persist. In West v. Van-Care. Inc. (Case No. CV-91-617), an Alabama jury returned a verdict for $65 million when an elderly male developed a 10 inch, gangrenous pressure ulcer while residing at the defendant's nursing home. There is therefore a need not only for better devices (e.g. mattresses) to prevent the formation of sores, but also a therapeutic composition that can be used in providing better skin care and accelerating the wound healing process in pressure ulcers.

(C) General and Plastic Surgery and Other Therapies

Surgery (including surgery for, but not limited to the following organs and tissues: skin, breast, chest wall, pleura, lung and mediastinum, heart disease, disease of great vessels, peripheral arterial disease, gastrointestinal disease, stomach, colon, rectum and anus, appendix, liver, gallbladder and extrahepatic biliary system, pancreas, spleen, peritonitis and intraabdominal infection, abdominal wall, omentum, mesentery, and retroperitenium, abdominal wall hernias, pituitary and adrenal, pediatric surgery, thyroid and parathyroid, urology, gynecology, neurosurgery, orthopedics, amputations, hand, plastic and reconstructive surgery, oncological surgery, head surgery, orthopedic, musculoskeletal, genitourinary system, pediatric, gastrointestinal), internal wounds, plastic surgery, gynecological surgery, scar removal, laser treatment, rentgen radiation, radioactive radiation, ozone treatment, or heat treatment, are some procedures that result in wounds that trigger the onset of host defenses. Host defenses against infection can be local or systemic, nonspecific or specific, and humoral or cellular. A variety of normal functions act continually to reduce the body's bacterial burden and to expedite the healing processes. The prophylactic and therapeutic compositions of the present invention can be used to accelerate or enhance the natural immunological phenomena involved in dealing with potential invading pathogens, for example the combined protective effects of anatomic barriers, baseline cellular phagocytosis, digestion by phagocytic cells or effector mechanisms.

(D) Burns

Burns are a very common injury, with estimates of at least two million individuals per year being burned severely enough to require medical attention. The classic description of first-, second-, third-, and fourth-degree bums is an anatomic one based on the depth of injury related to the skin anatomy. A first-degree bum has not penetrated the basal layer of the epithelium. In essence, the epithelium has not been breached. These injuries are typified by sunburns and essentially need little care, except possibly for a moisturizer. A second-degree burn extends from beneath the basal layer of the epithelium to, but not through, the entire epidermis. Epithelial cells lining the dermal adnexa remain viable and migrate to cover the surface of the wound. A third-degree burn extends completely beneath the dermis into the fat. A fourth-degree bum extends into muscle and bone and requires treatment in a specialized burn center. The therapeutic compositions of the present invention are suitable for accelerating wound healing in burn patients, in patients with inhalation injury, upper airways burns, lower airways burns or lung bums and in the management of related complications.

6. EXAMPLES

The present invention is exemplified herein by the use of microspheres which can be used to promote wound healing in general, as well as muscle regeneration. Wound healing and muscle regeneration both involve the repair of damaged tissue and the replacement of missing tissue. The migration and proliferation of specific types of cells must occur in an orderly and structured manner, which can be easily differentiated from the unrestrained growth of malignant tissues such as solid tumors. In particular, cells involved in wound healing and muscle repair must first become activated in order to perform their required roles in the healing process. Although the exact mechanism is not known, the orderly, structured cell growth in proliferation which occurs in wound healing clearly demonstrates the presence of a highly organized regulatory process.

As demonstrated in the Examples given below, the microspheres of the present invention do not appear to interfere with this complex, organized and structured process, since these microspheres clearly only quicken the pace of the overall healing process, as well as of specific steps within that process. However, unexpectedly the microspheres of the present invention do not cause the cells to exhibit a state of continuous, unrestrained metabolic activation, indicating that normal regulatory processes are not affected. Thus, the microspheres of the present invention do not cause unrestrained cellular activation.

Without limiting the present invention to a particular mechanism, the addition of microspheres with negatively charged groups may have a therapeutic effect on wound healing by serving as an additional surface for the attachment and plating of cells. One explanation for the efficacy of the microspheres of the present invention is that the negatively charged groups enable the creation of multiple links between the solid surface of the microsphere and the cell membranes, which represent multi-point contacts between the material of the microsphere and the cell membrane. The formation of these links causes changes in the distribution and state of membrane ligands, cytoskeletal reorganization, activation of intracellular signal transduction and other biochemical changes, eventually leading to activation of the cell. Cell activation then leads to cell proliferation and production of growth factors, and of collagen and other components of the extracellular matrix. It should be noted that the present invention need not rely on any particular mechanism, since as demonstrated below, these microspheres clearly had a beneficial effect for wound treatment and healing in vivo.

A number of different types of microspheres were tested in the Examples below. These microspheres were made of polystyrene, either with carboxyl or amino surface groups or without additional surface groups. The diameters of the microspheres ranged from about 0.1 to about 20 microns. The zeta potential of certain microspheres was also tested and demonstrated that the size of the sphere and the type of surface groups clearly had an effect on the amount of overall charge carried by each microsphere, which could have important effect on the ability of the microsphere to promote wound healing.

Although certain specific types of microspheres are illustrated, it is understood that many other related types of microspheres could be used if the following characteristics were fulfilled.

1. They should be capable of forming multi-point contacts with cells or portions of cells thereof;
2. Their mechanism of action should not require chemical alteration or degradation; and
3. They should be substantially insoluble in aqueous media such as bodily fluids, and instead should form a suspension.

Other preferable attributes include the following. First, the microspheres should preferably be made from material which is non-biodegradable during the treatment period, most preferably polystyrene. Second, the microspheres should preferably carry a substantial charge, more preferably an overall negative charge. Although the size of the microspheres is less critical, preferably the microspheres should be from about 0.1 to about 20 microns in diameter. Preferably, the microspheres should be derivatized with carboxyl surface groups, although other negatively charged groups may also be used. Thus, these types of microspheres are given for illustrative purposes only and are not meant to be limiting in any way. The principles and operation of microspheres according to the present invention may be better understood with reference to the Examples, drawings and the accompanying description.

Example I

Effect of Microspheres on Creatine Phosphokinase

Figure 1:
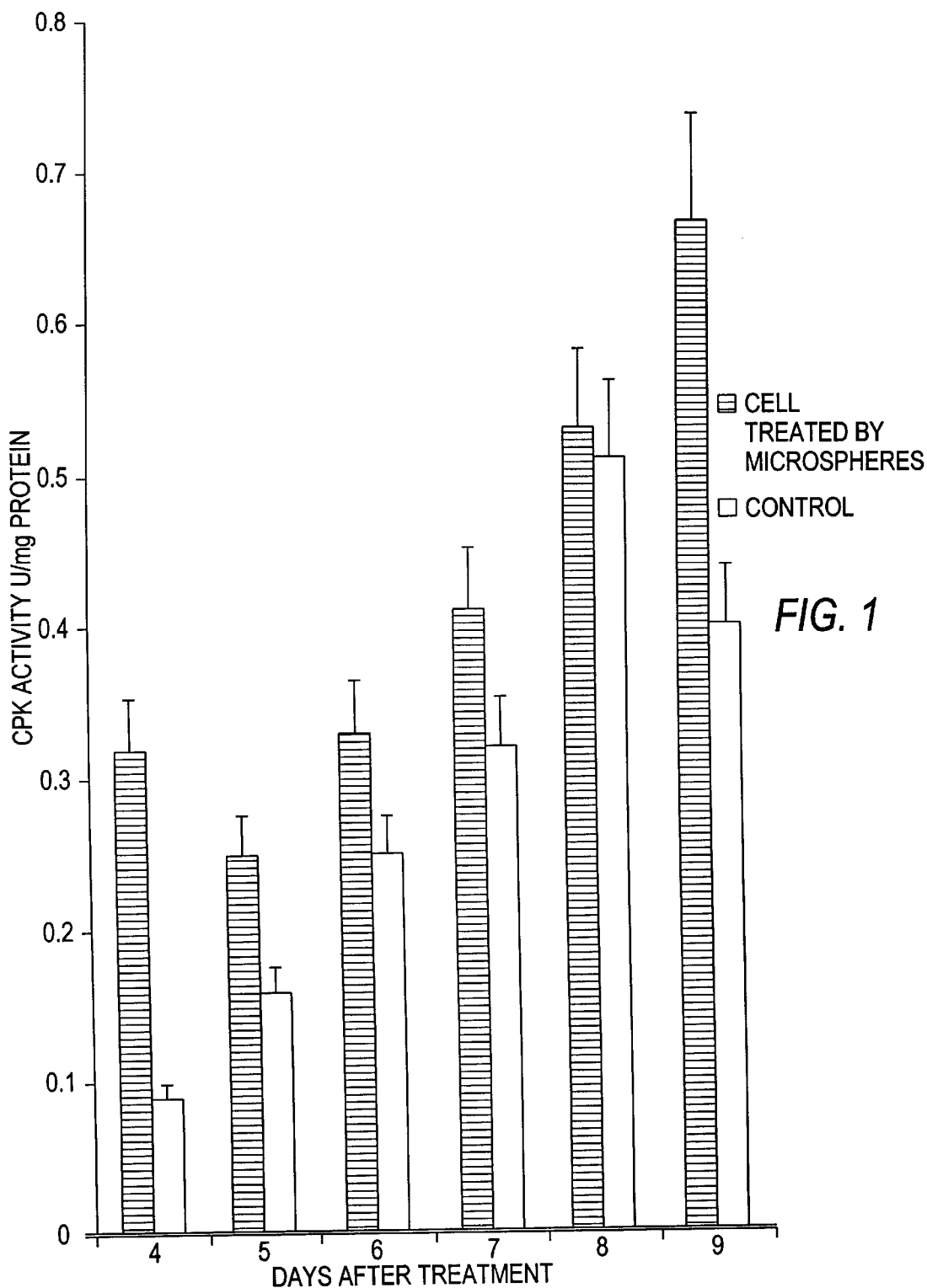
FIG. 1 is a graph showing the ability of the microspheres of the present invention to increase creatinine phosphokinase activity.

The microspheres of the present invention clearly induced an initial increase in creatine phosphokinase (CPK) activity of cultured myoblasts, as shown in FIG. 1. However, after eight days, the untreated and treated cells both demonstrate the same level of CPK activity, indicating that the induction of increased CPK activity by the microspheres of the present invention is temporary. The experimental method was as follows.

A primary culture of rat embryo skeletal muscle was prepared as described by Freshney [R. J. Freshney, *Culture of Animal Cells*, Willey. 1986, p. 117. 170–172]. Briefly, the muscles were dissected free of skin and bone and 15 desegregated by warm trypsinization (0.25% trypsin at 36.5° C.). Contamination by fibroblasts was reduced by preplating cells for 1 hour in an incubator with 5% $CO_2$, 37° C., since fibroblasts adhere to tissue culture plates first. Myoblasts were then seeded on 35 mm Petri dishes at a concentration of 5,.000 cells per ml with 2 ml of media (Dulbecco modified Eagle medium: medium 199 at a 1:4 ratio), enriched by antibiotics, 10% vol/vol horse serum and 4% vol/vol chick embryonic extract. The chick embryonic extract was prepared from 10 day-old chick embryos according to R. J. Freshney, *Culture of Animal Cells*, Willey, 1986. The antibiotics included amphotericin and gentamicin, diluted as 1:1000 from the standard initial concentration of 2.5 mg/ml. After 24 hours, the media was decanted and replaced with new media containing 20% vol/vol fetal horse serum and 1% vol/vol chick embryonic extract.

The cultured cells were then either treated with microspheres, starting at the time of plating, in media for 4–8 days or with media alone. The microspheres were either carboxylated polystyrene of 1, 2 or 4.5 microns in diameter, or polystyrene alone at 4.5 microns in diameter. The concentration of microspheres was either $10^6$ or $10^7$ per ml of media, with similar results obtained for both concentrations (not shown). After 4, 5, 6, 7 or 8 days of treatment, creatine phosphokinase activity was measured by a standard assay ("Creatine Kinase", *Worthington Enzyme Manual*, Worthington Biochemical Corporation, Freehold, N.J., USA, 1972. pp. 54–55). Results are shown in FIG. 1, as Units of CPK activity per mg of total cellular protein.

FIG. 1 clearly demonstrates the ability of the microspheres of the present invention to induce an initial increase of creatine phosphokinase activity, as compared to control cells. After 4 days of treatment, microsphere treated cells show an initial increase of CPK activity as compared to control cells. This increase is particularly pronounced at days 5 and 6 of treatment. However, by day 7, CPK activity in control cells is beginning to achieve parity with that of microsphere-treated cells. By day 8, both control and microsphere treated cells show similar levels of activity. Clearly microspheres promoted an initial increase of CPK activity in myoblasts, which leveled off after 8 days of treatment. Such increased CPK activity is correlated with biochemical maturation of myogenic cells. Thus, the microspheres promoted biochemical maturation of the cultured myoblasts.

Example 2

Effect of Microspheres on Cell Proliferation and Fusion

The microspheres of the present invention were demonstrated to induce an initial increase in both cell proliferation and myoblast fusion, as compared to control (untreated) cells, as shown below.

Primary cultures of rat myoblasts were prepared as described in Example 1 above, except that the cells were grown on cover slips. Treated cells were incubated with microspheres in media, as further described below, while control cells were only given media To determine the extent of cell proliferation, cells were fixed in ethanol/acetic acid (3:1) and then stained by hematoxilin-eosin. The stained cells were then counted in a light microscope. The mitotic index was calculated as the proportion of cells in mitosis counted per 1000 cells.

For the examination of cell proliferation, polystyrene microspheres which had sulfate surface groups were used, with a diameter of 0.18 microns, and a concentration of $10^7$ microspheres/ml of media. A 20-fold increase in the mitotic index was observed after treatment for 24 hours with microspheres as compared to control cells. Specifically, the mitotic index of control cells was 1.25+0.7%, while that of microsphere-treated cells was 24.6+1.0%. Thus, clearly microspheres promoted a large increase in the mitotic index of the myoblasts.

The effect of microspheres on myoblast fusion was also examined. Results are given in Table 1. Generally, cells treated with microspheres exhibited about 150% fusion rate as compared to controls. However, the extent of this effect depended upon the type of microspheres and the length of treatment.

The types of microspheres tested are given in Table 1. The diameter of the microspheres is given in microns under "Diameter". The surface groups on the polystyrene beads are given under "Surface Group". Polystyrene beads without any further derivatization are "polystyrene". Beads derivatized with either carboxyl or amino surface groups are described as "carboxy" and "amino", respectively. The concentration of beads is given as number of beads per ml of media under "Conc."

Cells were prepared, fixed and stained as for determining the rate of proliferation of myoblasts, described above. Cells were initially plated at the density given in Table 1 as cells per ml media, under the column "Initial Cells". The measurements of myoblast fusion were made after the given number of days after treatment under "Days after Treatment".

The extent of fusion is calculated as the proportion of nuclei within multinuclear cells, or myoimplants, related to the total amount of nuclei within the microscopic field, given as "Proportion of Fusion" for microsphere treated cells, and "Control Fusion" for control, untreated cells. At least 400 nuclei were counted for each experimental condition. The ratio of the extent of fusion in microsphere treated cells and control, untreated cells is given as "Relative Effect". If no value is given for a particular slot in Table 1, the value is the same as that in the row above.

blast fusion occurs when muscle tissue is formed during embryogenesis, and is also a very important step in muscle regeneration and repair of damaged muscle tissue. Thus, the ability of microspheres to promote such fusion clearly indicates the potential of these microspheres to promote muscle regeneration, as demonstrated in Example 5 below:

Example 3

Effect of Microspheres on Collagen Synthesis and Deposition

As noted above in the Background section, collagen synthesis and deposition is an important step in the process of wound healing. Furthermore, the amount of collagen deposited in the !wound is an important determinant of wound strength. Thus, although the microspheres of the present invention clearly have a variety of effects on different cell types, as demonstrated in the preceding and following Examples, clearly one important determinant of the ability of a composition to promote wound healing is its effect on collagen synthesis and deposition.

Figure 2A:
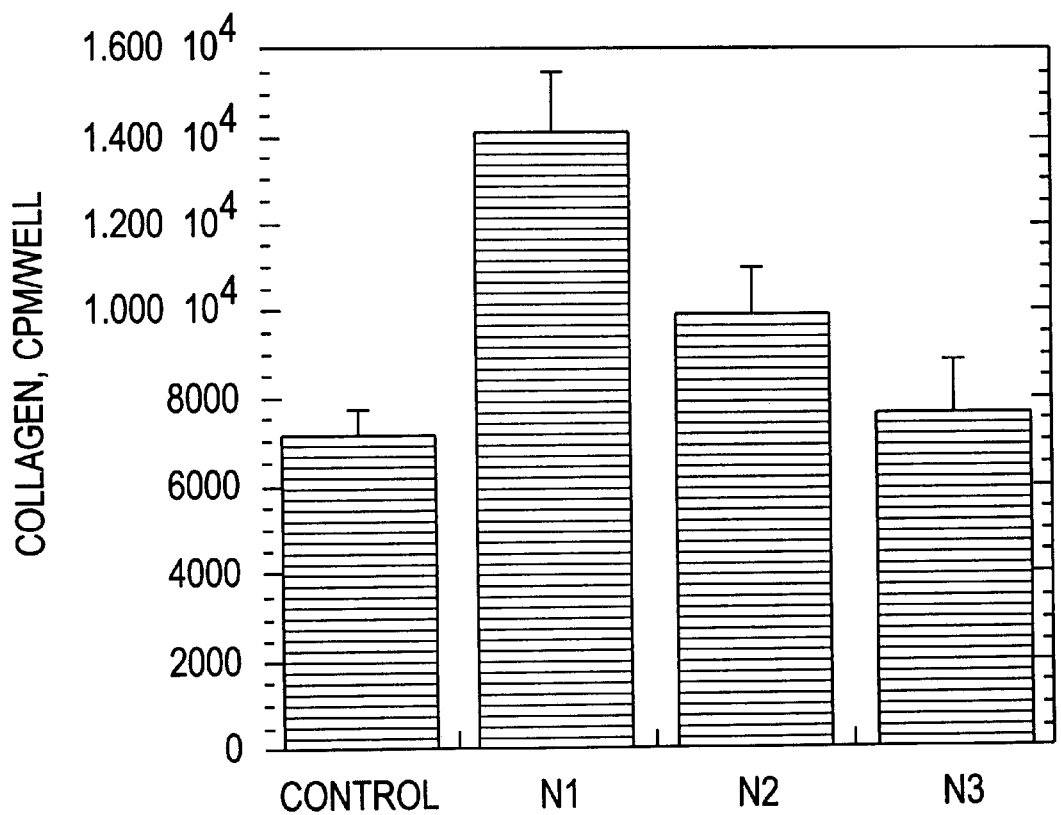
FIG. 2 is a plot illustrating the effect of the microspheres of the present invention on collagen synthesis.
Figure 2B:
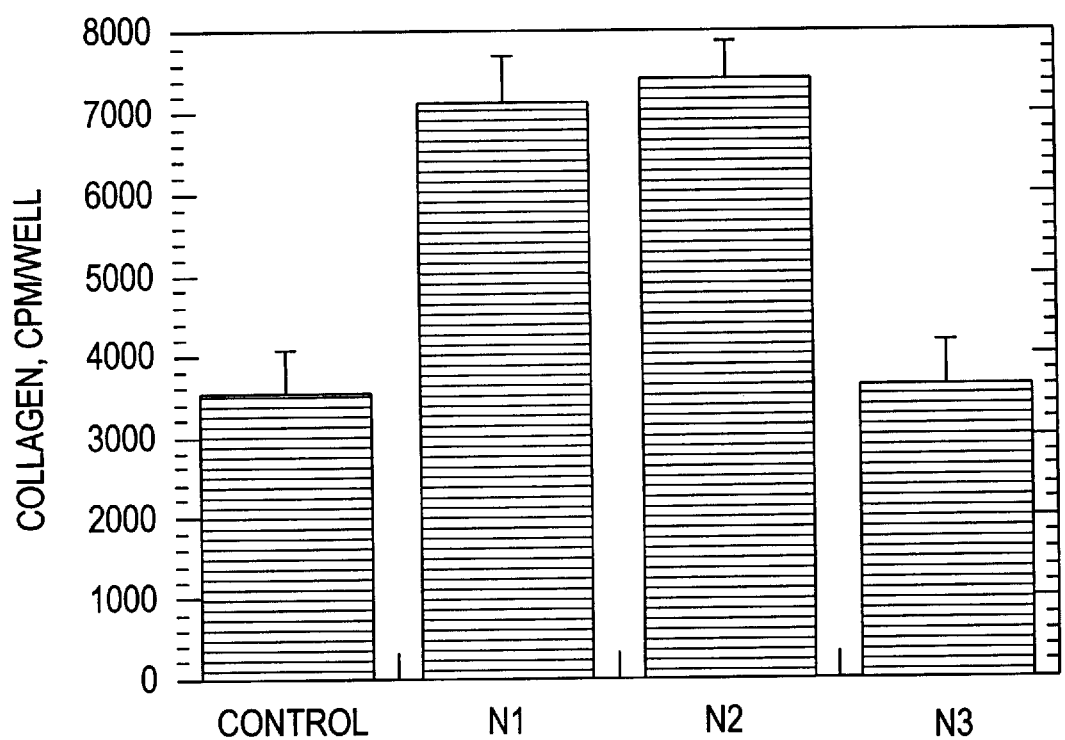

As shown in FIGS. 2A and 2B, the microspheres of the present invention clearly promote collagen synthesis by cultured fibroblasts. The largest effect is seen with Type I and Type II microspheres. Type I microspheres had a diameter of 4.5 microns, was made of carboxylated polystyrene and had a Z potential of about −29.96 mV. Type II microspheres had a diameter of 0.49 microns, were made of polystyrene alone and had a Z potential of about −34.5 mV. Type III microspheres had a diameter of 1.0 microns, were made of carboxylated polystyrene and had a Z potential of about −53.34 mV. The experimental method was as follows.

Foreskin fibroblast cultures were grown in 75 $cm^2$ plastic flasks (Corming Glass Works, Corning, N.Y.) in Dulbecco's modified Eagle medium (DMEM) containing 4.5 mg/ml glucose supplemented with 10% vol/vol fetal calf serum, 2 mM L-glutamine, 50 ug/ml gentamycin sulfate and 2.5 mg/ml amphotericin B. The cultures were incubated at 37° C. in 5% $CO_2$ until confluent. Fibroblasts were harvested

TABLE 1

Effect of Microspheres on Fusion Myoblasts

| Diameter | Surface Group | Conc. | Initial Cells | Days after Treatment | Proportion of Fusion | Control Fusion | Relative Enhancement |
|---|---|---|---|---|---|---|---|
| 0.22 | polystyrene | $10^7$ | $3*10^4$ | 6 | 0.75 ± 0.06 | 0.58 ± 0.10 | 1.29 |
|  |  |  |  | 7 | 0.82 ± 0.09 | 0.64 ± 0.09 | 1.28 |
| 0.49 |  |  |  | 6 | 0.86 ± 0.06 | 0.58 ± 0.10 | 1.48 |
|  |  |  |  | 7 | 0.91 ± 0.07 | 0.64 ± 0.09 | 1.57 |
| 0.91 | carboxy | $10^8$ | $5*10^5$ | 5 | 0.84 ± 0.06 | 0.64 ± 0.09 | 1.31 |
|  |  |  |  | 4 | 0.63 ± 0.09 | 0.51 ± 0.06 | 1.23 |
| 1.12 | amino |  | $4*10^4$ | 6 | 0.69 ± 0.15 | 0.58 ± 0.10 | 1.18 |
|  |  |  |  |  | 0.73 ± 0.08 | 0.58 ± 0.10 | 1.25 |
| 2.01 | carboxy | $10^7$ | $5*10^5$ | 5 | 0.84 ± 0.096 | 0.64 ± 0.09 | 1.31 |
|  |  |  |  | 4 | 0.63 ± 0.06 | 0.51 ± 0.06 | 1.23 |
| 4.58 |  | $10^6$ |  | 5 | 0.72 ± 0.09 | 0.64 ± 0.09 | 1.12 |
|  |  |  |  | 4 | 0.67 ± 0.09 | 0.51 ± 0.09 | 1.31 |
| 10.85 |  |  |  | 5 | 0.68 ± 0.08 | 0.64 ± 0.09 | 1.06 |
|  |  |  |  | 4 | 0.60 ± 0.10 | 0.51 ± 0.09 | 1.17 |

As can be seen from Table 1, all of the different types of microspheres promoted myoblast cell fusion, although the extent of the effect depended upon the diameter of the microsphere, the surface group on the microsphere, the number of days after treatment and the concentration. Myousing 0.25% trypsin/0.05% EDTA solution and subcultured in 24-well plates at a density of 200.000 cells/well with the same media for 24 hours, at which time treated cells were incubated with Type I, II or III microspheres. Control cells were incubated with media alone.

Collagen synthesis was measured as follows. The cultured fibroblasts were preincubated in DMEM supplemented with 0.5% dialyzed fetal calf serum for 24 hours. Cells were labeled with 3 uCi 2,3-$^3$H-proline or 3,4-$^3$H-proline solution containing B-aminopropionitrile famarate (BAPN) at a final concentration of 100 uM, in the presence (FIG. 2A) or absence (FIG. 2B) of 10 uM ascorbic acid as indicated. Ascorbic acid promotes collagen synthesis in fibroblasts and is an important stimulation factor.

After 24 hours of incubation the reaction was terminated and collagen was extracted from each well by the addition of 30 uI cold acetic acid (0.5 M) containing pepsin (final concentration 0.5 mg/ml), followed by gentle shaking at room temperature for 4 hours. After centrifugation, the cellular debris was discarded and 80 ul of collagen solution in 0.5 M acetic acid was added to each supernatant, with a final collagen concentration of about 200 mg/ml. Collagen was precipitated from each supernatant by the addition of 0.4 ml of 5.2M NaCI solution in 0.5 M acetic acid. After standing for 2 hours. precipitated collagen was separated by centrifugation for 15 minutes at 15,000 rpm. Next, the pellet was resuspended in 750 ul of 10 mM TRIS buffer, pH 7.4 containing 1 M NaCI. Collagen was precipitated by the addition of 750 ul TRIS buffer, pH 7.4 containing 5 M NaCI. After 2 hours the collagen was separated by centrifugation, redissolved in 0.5 M acetic acid and each sample was measured in a scintillation counter. Results are shown in FIGS. 2A and 2B, given as cpm per well. Data presented are an average of quadruplicate samples.

Both Type I and Type II microspheres were able to stimulate collagen synthesis above the level seen in control (untreated) fibroblasts, both in the presence (FIG. 2A) and absence (FIG. 2B) of ascorbic acid. Type I microspheres had a greater effect relative to Type II microspheres in the presence of ascorbic acid, although both types had a similar effect, in the absence of ascorbic acid. Type III microspheres did not have a detectable effect on collagen synthesis either in the presence or absence of ascorbic acid.

One particularly interesting finding is that both Type I and Type II microspheres had an effect, while Type III microspheres did not, indicating that the specific size and material of the microspheres is important. Furthermore, both Type I and Type II microspheres elicited an effect even in the absence of ascorbic acid, indicating that these two types of microspheres can potentiate collagen synthesis even in the absence of other stimulatory factors. Thus, clearly both Type I and Type II microspheres have a substantial stimulatory effect on collagen synthesis.

Example 4

Effect of Microspheres on Myoblast Shape

Primary cell cultures of rat myoblasts were prepared as described in Example 1 above. Cells were then incubated with polystyrene microspheres (treated cells) or without (control cells) for 48 hours. Cells were then fixed in 1% glutaraldehyde in phosphate buffered saline for 1–4 days, and rinsed in PBS. Cells were then transferred to a solution of 1% tannic acid and 1% guanidine HCI (1:1 ratio) in PBS for 1 hour. Specimens were post-fixed in 1% $OSO_4$ for 1 hour and dehydrated in graded ethanol and Freon 113 at room temperature. Specimens were then mounted on slides, coated with gold and examined in a JEOL T-300 scanning electron microscope at 2 kV.

Figure 3A:
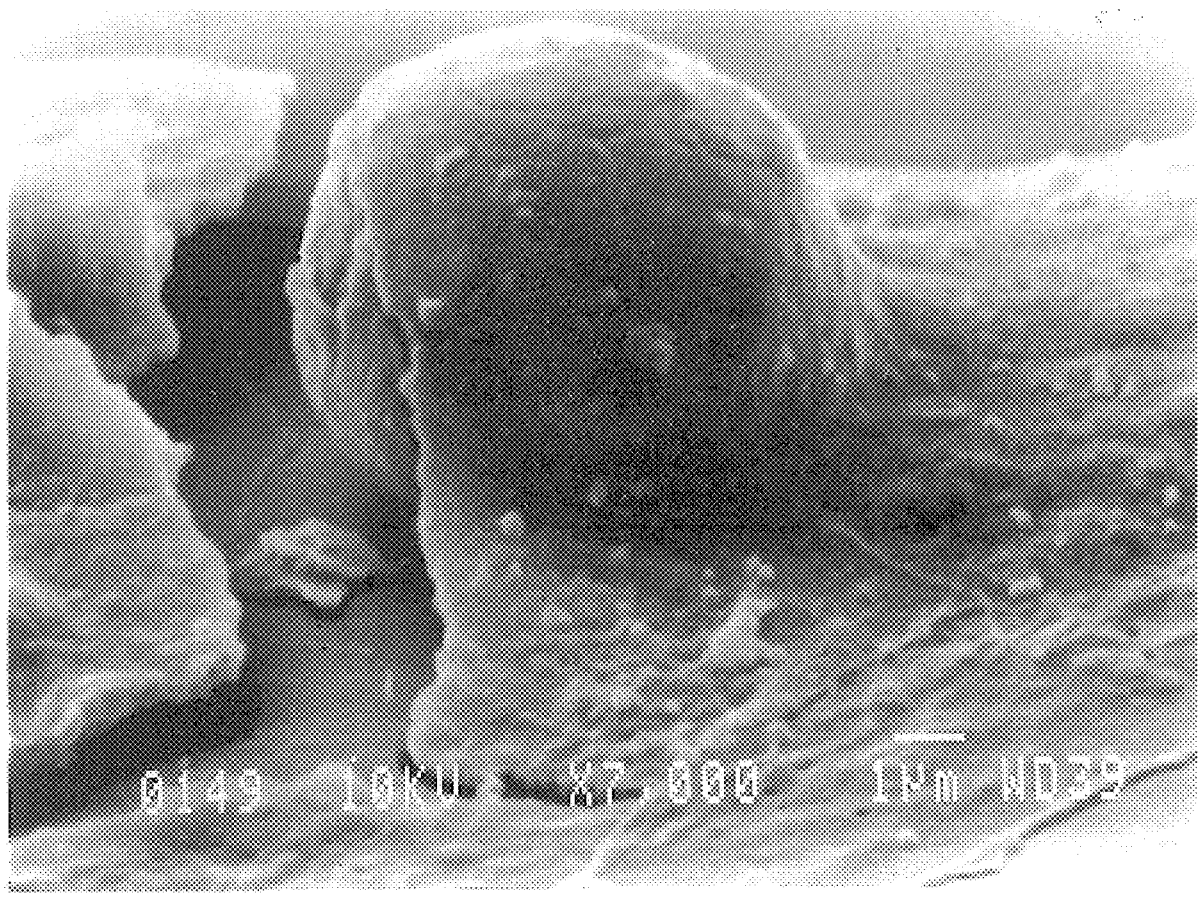
FIGS. 3A–3C illustrate the effect of the microspheres of the present invention on myoblast shape.
Figure 3B:
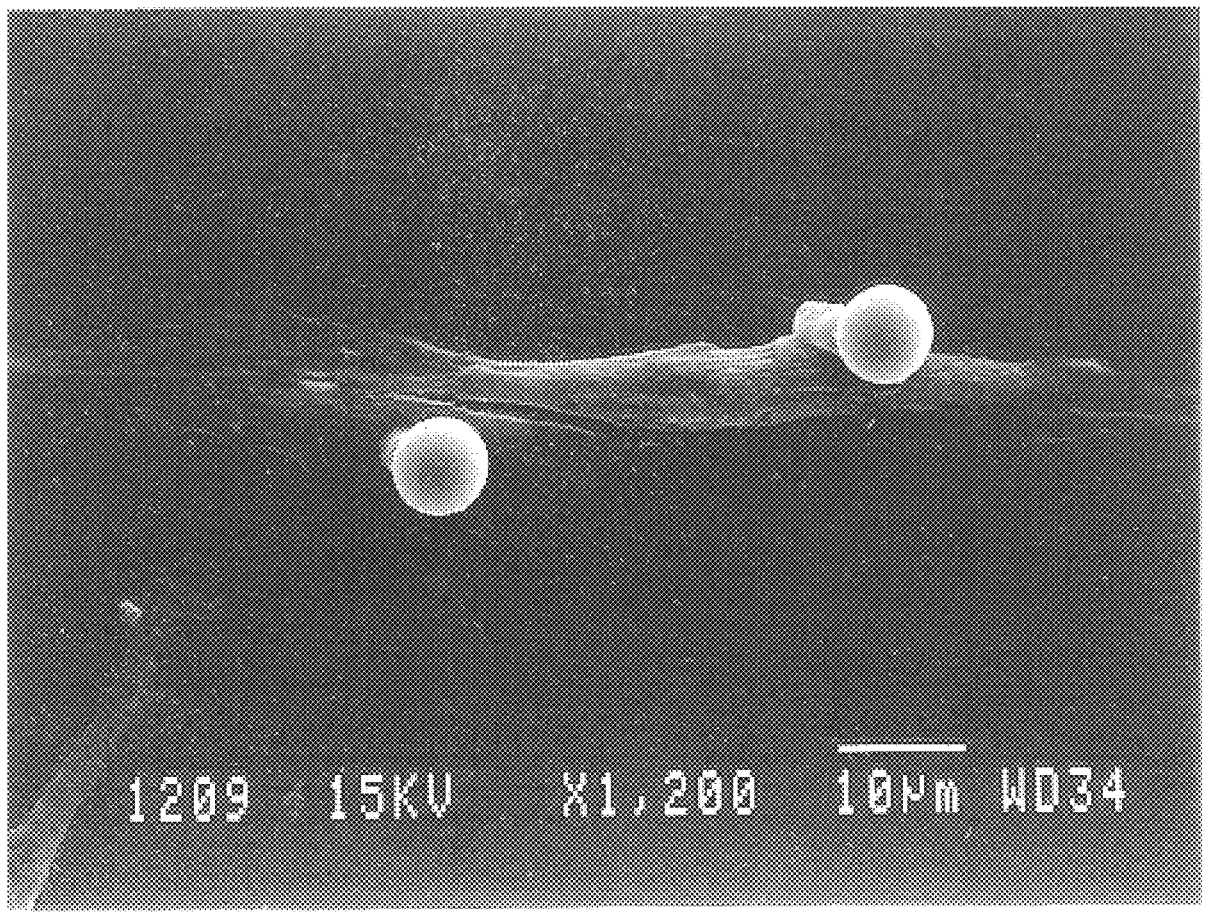
Figure 3C:
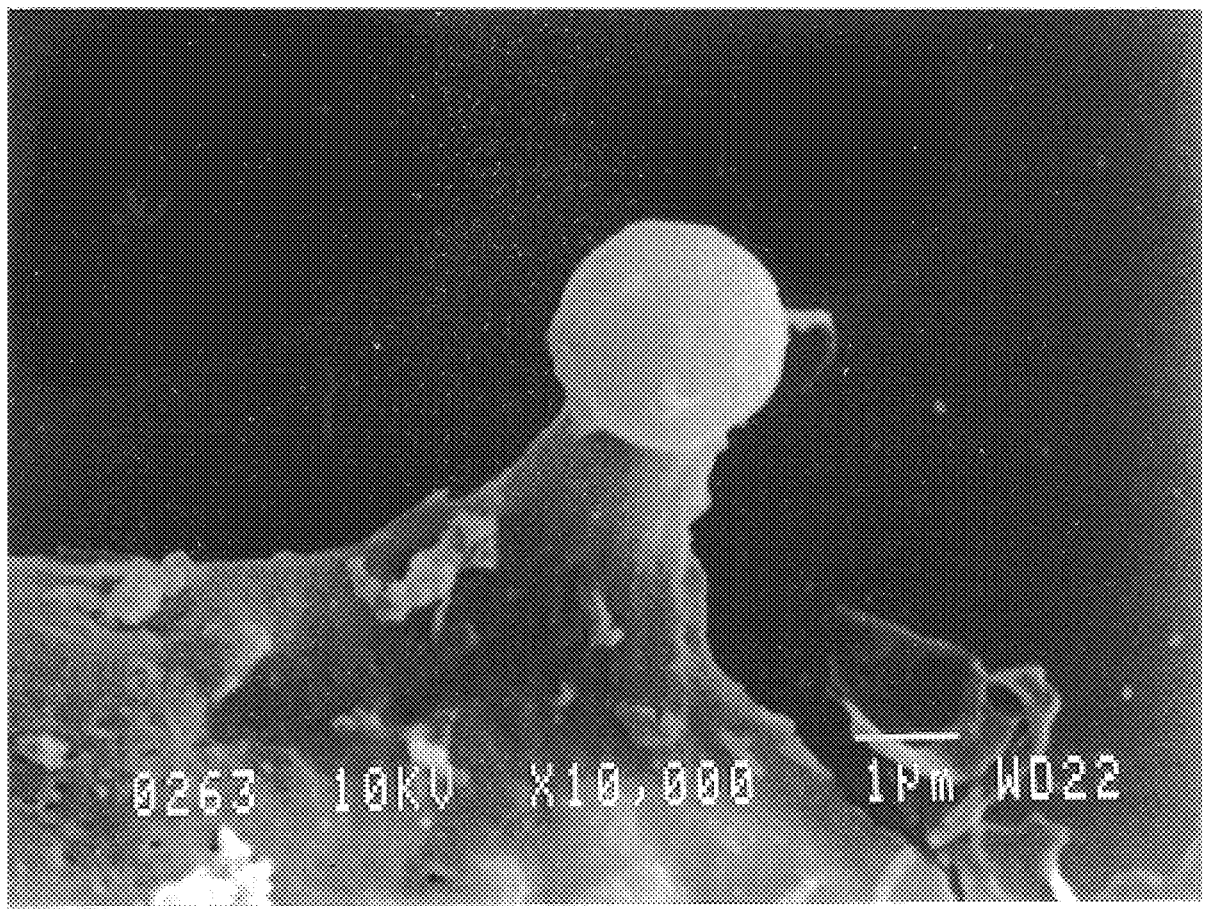

FIGS. 3A–3C illustrate the effect of the microspheres of the present invention on myoblast shape. The cell in FIG. 3A has grown over the microsphere so that part of the cell surface is convex rather than flat. FIGS. 3B and 3C show cells extending pseudopodia from a portion of the cell on which the microsphere rests. The pseudopod of the cell in FIG. 3C is particularly pronounced, showing that the microspheres clearly influence myoblast shape. Furthermore, the formation and extension of a pseudopod clearly requires changes in the cytoskeletal structure, demonstrating that the microspheres also affect the cytoskeleton of the cell. The formation of such pseudopodia may be important for the migration of cells into the wound area. Thus, the stimulation of such pseudopodia by the microspheres indicates their ability to promote another important step in the wound healing process.

Example 5

Compositions and Methods for Application

The following description is a general device and method for application of the agents for wound healing. The agents, such as microspheres, are preferably applied repeatedly to the wound to be treated. The frequency of application, and the concentration applied, is dependent on the severity of the symptoms and on the responsiveness of the subject to the treatment. Persons of ordinary skill in the art can easily determine optimum concentrations, dosing methodologies and repetition rates. In the present study, the microspheres were applied to the wound to be treated about once per day, although of course other application rates are possible.

The method includes the step of administering the agents such as microspheres, in a pharmaceutically acceptable carrier in which the agents are substantially insoluble, to a subject to be treated. Examples of pharmaceutically acceptable carriers include aqueous media for a suspension of agents, non aqueous media such as ointments, creams and aerosol-forming material, as well as bandages soaked in, or otherwise containing, media with the agents. The bandages can be occlusive or non-occlusive. In any case, the agents which are in a pharmaceutically acceptable carrier can be described as a dispersion of agents.

The agents are administered according to an effective dosing methodology, preferably until a predefined endpoint is reached, such as the absence of clinical symptoms in the subject. The closure of the wound to be treated is an example of such an endpoint.

The device of the present invention includes a composition with one or more agents and a pharmaceutically acceptable carrier for the agents, and a container for containing the composition. Examples of suitable containers include aerosol-dispersing pumps and spray cans. One of ordinary skill in the art could easily select suitable containers for the composition. Regardless of the particular device used, the agents, such as microspheres, are preferably applied in a two step procedure. The microspheres are first applied in a dispersion to the wound, by dripping, spraying, painting, washing or by any other suitable method of topical application. Preferably, 30 sec to 2 minutes are allowed to elapse before the second step, in order to allow the microspheres to form initial contact with the wound. Preferably, the second step includes applying an occlusive or non-occlusive bandage, or other suitable covering soaked in the liquid suspension containing the microspheres, to the wound. This substantially reduces or eliminates absorption of the microspheres by the bandage or covering. This method was used both in rats and humans for wound healing as described in the Examples below.

The microspheres in the suspension did not aggregate, coalesce, clump or undergo irreversible caking. Although the microspheres did settle somewhat over time, they were easily resuspended with gentle agitation.

Example 6

Promotion of Wound Healing in Rats by Microspheres

As noted above in Examples 1–4, the microspheres of the present invention promote various in vitro cell processes which are important for wound healing. However, in vitro and in vivo effects do not always correlate.

Therefore, in vivo experiments were performed to assess the ability of the microspheres to promote wound healing in rats. As shown in FIGS. 4A–4D, the microspheres of the present invention clearly promote wound healing in rats. FIG. 5 is a graph of the rate at which the wound area decreases, showing that the microspheres of the present invention increase the rate at which such a decrease occurs. Finally, Table 2 shows that the microspheres promote muscle regeneration in rats. The experimental method was as follows.

Male Wistar rats, weighing between 300 and 400 g, were anesthetized by nembutal (5 mg/kg of body weight). An excision injury to the lateral parts of the Tibialis anterior muscle was performed as follows. First, a longitudinal incision was made in the skin to expose the Tibialis anterior muscle. Next, the partial excision of this muscle was made by a transverse cut of the muscle fibers, along about half of the muscle width. The excised piece was then cut out of the muscle, leaving a gap of about 5 mm by 5 mm in the muscle. In all rats the same amount of excised tissue (80±10 mg) was removed from precisely the same location in the muscle. The wound area was then dressed with 2 micron polystyrene microspheres in saline for treated rats, and saline alone for control rats. The wound area was measured for between 3 and 15 days following injury.

Figure 4A:
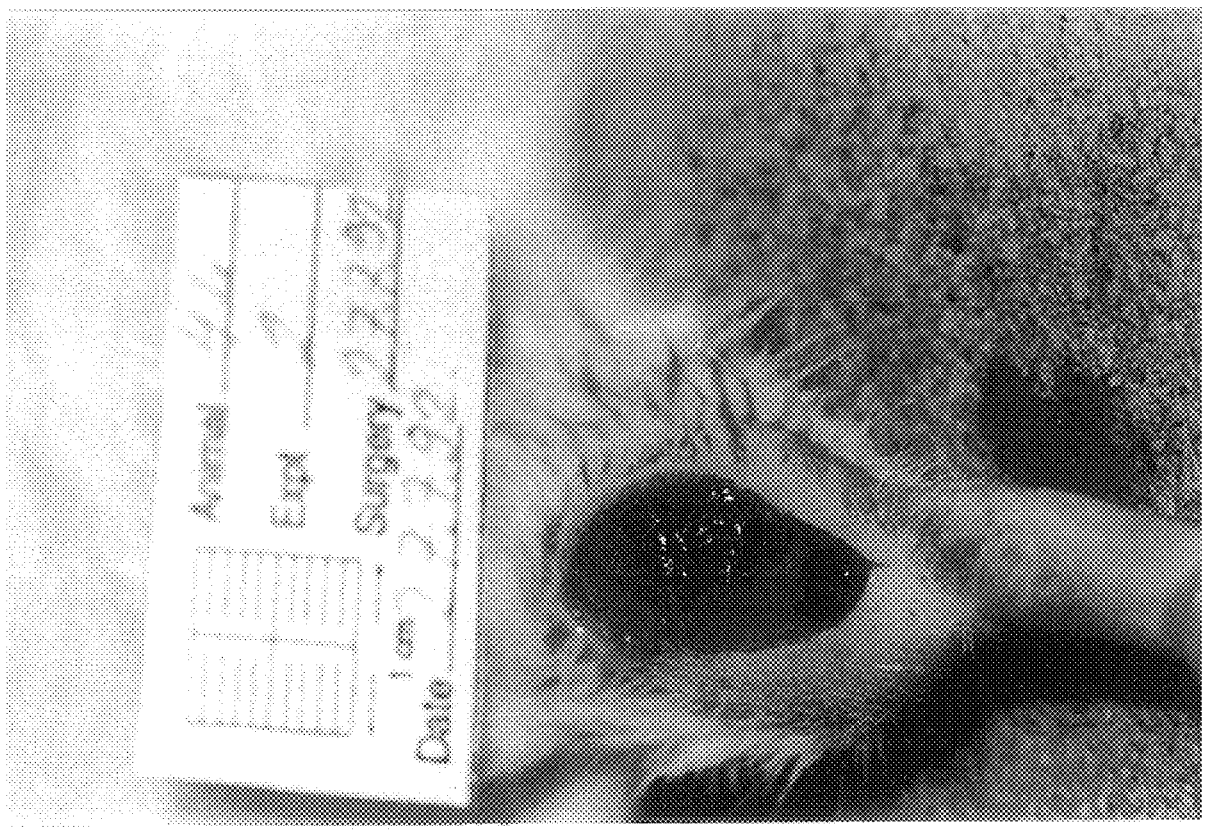
Figure 4B:
Figure 5:
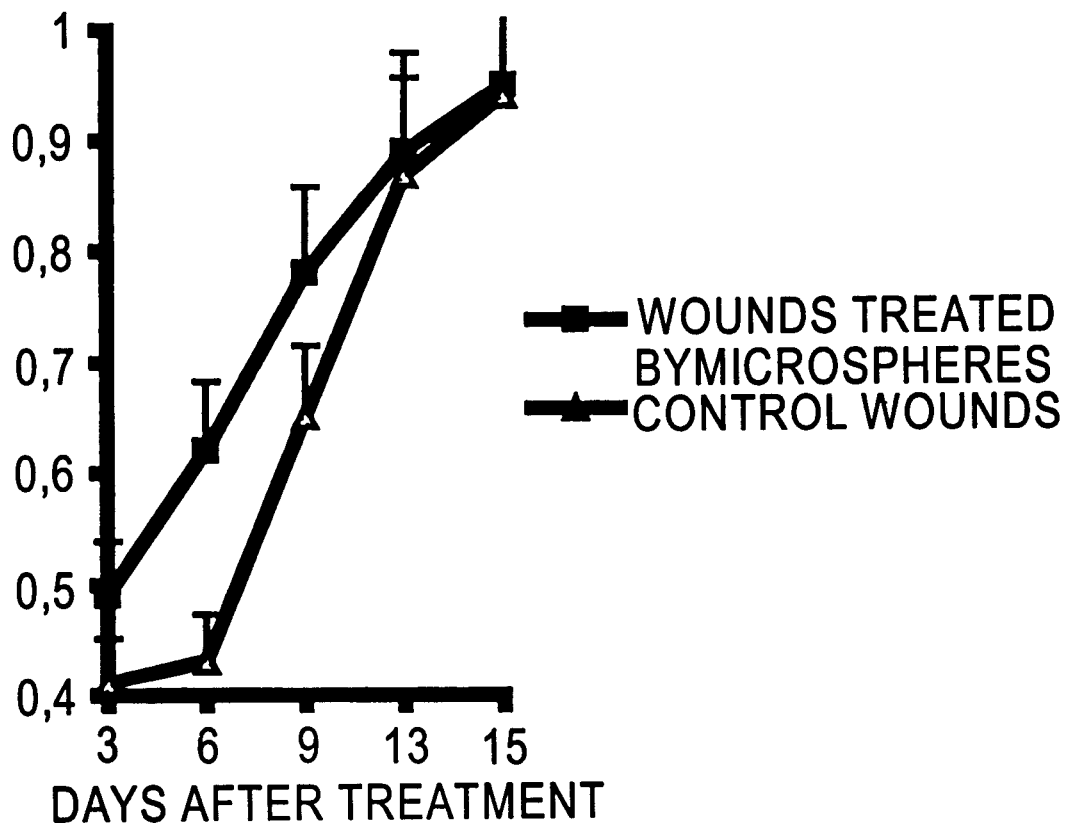
FIG. 5 is a graph at the rate at which wound area of FIG. 4 decreases.

FIGS. 4A–4D show pictures of wound areas prepared as described above. FIG. 4A shows the wound of the control rat immediately after injury, while FIG. 4B shows the equivalent wound of the rat to be treated. FIGS. 4C and 4D show the same rats five days after injury. The wound of the control rat was treated with saline alone, and still has not completely healed. By contrast, the wound of the treated rat, treated with microspheres, has completely healed. Thus, clearly the microspheres of the present invention promote faster wound healing.

FIG. 5 further illustrates the promotion of wound healing by the microspheres of the present invention. The wounds of control rats eventually heal, but at a much slower rate than the wounds of treated rats. Thus, the microspheres clearly increase the rate at which the wound area decreases and the wound heals.

Slides were prepared for histological analysis by making a biopsy punch of the wound area. Rats were sacrificed 4, 5, 6, 7, 8, 9, 13 or 14 days after injury and biopsies were taken for histological examination. The number of specialized myogenic cells incorporated into the newly formed or repaired muscle fibers was counted by determining the number of "new" nuclei, which represent activated myogenic cells. The nuclei of these cells are large, basophilic nuclei with dispersed chromatin and can be easily differentiated from the nuclei of existing myoblasts. Results are given in Table 2.

TABLE 2

Promotion of Muscle Regeneration by Microspheres

| Treatment | Post-Surgical Day | "New" Nuclei Per Slide | "New" Nuclei Per Field | "New" Nuclei Per Fiber |
|---|---|---|---|---|
| M | 4 | 422 ± 67 | 53.8 ± 22 | 9.5 ± 3.5 |
| C | 4 | 117 ± 37 | 14.6 ± 10 | 5.9 ± 1.4 |
| M | 5 | 350 ± 84 | 43.8 ± 13.5 | 8.6 ± 1.8 |
| C | 5 | 110 ± 31 | 14.1 ± 4.6 | 4.8 ± 1.2 |
| M | 6 | 1221 ± 180 | 94 ± 25 | 11.9 ± 5 |
| C | 6 | 676 ± 120 | 52 ± 11 | 4.9 ± 0.9 |
| M | 7 | 762 ± 110 | 95 ± 51 | 9.4 ± 3.5 |
| C | 7 | 169 ± 47 | 21.1 ± 4.8 | 4.5 ± 0.8 |
| M | 8 | 715 ± 140 | 89.4 ± 36 | 11 ± 2.2 |
| C | 8 | 126 ± 32 | 18.6 ± 12 | 5.2 ± 1.5 |
| M | 9 | 299 ± 75 | 42.7 ± 19 | 7.4 ± 1.3 |
| C | 9 | 235 ± 84 | 33 ± 12 | 6.5 ± 2.8 |
| M | 13 | 747 ± 129 | 53.3 ± 15 | 9.7 ± 1.5 |
| C | 13 | 582 ± 140 | 42 ± 42 | 5 ± 1.7 |
| M | 14 | 665 ± 143 | 83 ± 24 | 9.4 ± 1.9 |
| C | 14 | 491 ± 124 | 61 ± 36 | 5.5 ± 2.7 |

As shown in Table 2, the microspheres of the present invention clearly promoted muscle regeneration, as measured by the number of "new" or incorporated nuclei in muscle fibers. The fact that such measurements were made on histological samples taken from rats treated in vivo also indicates that the microspheres promote muscle regeneration in vivo as well as in vitro. Finally, FIG. 6 compares the effect of the microspheres of the present invention on wound healing with tissue culture media and saline in rats, wounds were induced in rats as described above, and the rats were treated with saline alone (FIG. 6A,), tissue culture media alone (FIG. 6B, x) saline plus microspheres (FIG. 6A,) or tissue culture media plus microspheres (FIG. 6B,). The rats were then photographed 4 days after wounding occurred. As can be seen from FIGS. 6A and 6B, the microspheres were able to induce a much more rapid rate of wound healing regardless of whether the carrier was saline or tissue culture media. Thus, tissue culture media was not responsible for any part of the effect of the microspheres of the present invention on wound healing.

Example 7

Toxicity Studies of Microspheres

No toxic effect of a preparation containing microspheres was observed. Preliminary examination of treated rats 65 and 180 days after injury showed that none of the following organs exhibited signs of pathological changes: heart, liver, lungs, kidney, blood vessels, stomach, lymph nodes and brain. Experiments with fluorescently-labeled microspheres showed that no signs of pathology were observed in treated rats. Furthermore, the microspheres did not penetrate into any of the above-referenced organs. No new growth was detected in the above-referenced organs. Finally, the microspheres were dispersed within the wound area but did not penetrate into regenerating muscle fibers.

Example 8

Effect of Microspheres on Wound Healing in Humans

The in vivo experiments described in Example 6 above clearly demonstrate that the microspheres of the present invention can promote wound healing and muscle regeneration in rats. Furthermore, the results of the toxicity studies in rats described in Example 7 show that the microspheres are substantially non-toxic. Therefore, studies were performed to determine the effect of the microspheres of the present invention on wound healing in humans. As described in detail below, case studies demonstrated that the microspheres clearly promoted wound healing in humans. The first case study was that of a 66-year old female with ulcers in the left leg which refused to heal. The patient also had cellulitis of the left leg and varicose veins in both legs. Ulcers on the inner thigh of the patient were treated with Milton 2% which is a corrosive chlorine salt in water. Ulcers on the outer thigh of the patient were treated with 4.5 micron microspheres of the present invention made from polystyrene in tissue culture medium. FIG. 7A shows the control wound at day 0, while FIG. 7B shows the control wound after 4 months of treatment. FIG. 7C shows the treated wound at day 0, while FIG. 7D shows the treated wound after 4 months of treatment. Both the wounds treated with the microspheres of the present invention and those treated with Milton exhibited signs of infection and other difficulties healing during the next four months. However, at the end of the treatment period, the wounds treated with microspheres had shown a significant improvement. The wound size had decreased and the wounds were clean, without signs of infection. Thus, even for wounds which were difficult to heal, due to complications such as infection, the microspheres of the present invention exhibited greater efficacy in wound healing promotion than currently available treatments.

As a further proof, the wound which had served as a control for FIG. 7 above (FIGS. 7A and 7B) was treated with the same microspheres as those used to treat the wound in FIGS. 7C and 7D. The results are shown in FIGS. 8A and 8B. FIG. 8A shows the wound at day 0 of treatment with microspheres, while FIG. 8B shows the wound after 21 days of treatment. Clearly, the extent of the wound has decreased, even after such a short time period. Furthermore, the wound was superficial and clean and as no longer producing exudations.

The second case study w as that of a 52-year old female who had a year old infected wound on the front side of the left thigh. The wound was treated with 1% Milton for a week, debrided and then treated with the microspheres of FIGS. 7 and 8 for 10 days. FIG. 9A shows the wound at day 0 of treatment, while FIG. 9B shows the wound after 10 days of treatment.

After 10 days, the wound showed a significant improvement. It had decreased in extent to a small size, was clean and was no longer producing exudations, as can be seen from FIG. 9B. Although the wound did not fully close during the relatively short treatment period, its effects had been significantly ameliorated.

The third case study was that of a 19-year old male who was injured by a chemical spill in an industrial workplace accident. The chemicals in question, sulfurides, caused severe bums and blistering on the right side of his neck and right hand. For the first two days, all wounds were treated with Silverol, a hydrogel with strong absorptive properties. Next, the wounds on the right forearm were treated with the microspheres of case studies 1 and 2, while the remaining wounds were treated with Silverol. The results are shown in FIGS. 10A and 10B (control wound at day 0 and day 5, respectively), and in FIGS. 10C and 10D (treated wound at day 0 and day 5, respectively).

After 5 days of treatment with microspheres, the condition of the treated wound on the forearm had improved significantly over that of the remaining wounds which were not treated with microspheres. The wound on the forearm had completely healed after 5 days of treatment with microspheres. By contrast, the remaining wounds which were treated with Silverol had not healed completely. Thus, the microspheres clearly promoted wound healing, demonstrating a greater efficacy than currently available treatments.

The fourth case study was of a 52-year old female who had sustained second-degree burns on the buttocks from a hot bath. Wounds on the left buttock were treated with Silverol, while those on the right buttock were treated with microspheres of the previous case studies. The results are shown, for microsphere-treated wounds only, in FIGS. 11A (day 0) and 11B (day 7) of treatment.

Seven days after beginning treatment, the wounds on the right buttock, which were treated with microspheres, had completely healed with good epithelial growth. By contrast, the wounds on the left buttock, which were treated with Silverol, had not completely healed and were closing relatively slowly. Thus, the microspheres were able to promote wound healing at a more rapid rate than conventional treatments.

The fifth case study was of a 28 year old female who had suffered extensive and severe sunburn (data not shown). She was treated with the microspheres of the previous case studies. The patient reported both a significant reduction in discomfort and rapid healing of the sunburn. Thus, the microspheres used in the method and device of the present invention can both relieve discomfort and promote wound healing, although it should be noted that the relief of discomfort is probably a highly indirect effect of the microspheres rather than direct analgesia.

Indeed, it is worth mentioning that the above patient report can only be inferred to include the apparent reduction in the sensation of discomfort from the sunburn. Such decreased discomfort probably does not demonstrate any ability of the microspheres to have a direct effect on the transmission of nerve impulses, or indeed to directly alter any of the many factors which lead to the sensation of discomfort. Instead, this effect is probably highly indirect, occurring as a result of the activation of macrophages, which in turn has anti inflammatory effects, leading to the decreased sensation of discomfort by the patient.

From these five case histories, coupled with the extensive evidence obtained from studies in rats, the use of the agents, such as microspheres, according to the present invention has clearly been shown to have greater efficacy for the promotion of wound healing and muscle regeneration than currently available, prior art treatments. The method and device promotes, accelerates and enhances wound healing, as well as diminishing discomfort experienced by the subject.

With regard to the diminished discomfort, it should be noted that the patients in the above case studies also reported local reduction in pain and discomfort from the treated wounds, particularly the patient suffering from sunburn, probably an indirect effect of the microspheres through their (also indirect) anti-inflammatory action.

Finally, although the data is not shown, an indirect bacteriostatic effect against infections of the wounds by Pseudomonas species was also noted in humans. The mechanism for both the indirect anti-inflammatory action and the indirect bacteriostatic effect is not clear, but is probably a result of a cellular effect involving the attraction and activation of macrophages. Regardless of the exact mechanism, the use of the microspheres according to the present invention clearly represents a significant improvement in the treatment of wounds.

Example 9

Effect of Microspheres on Wound Healing after radiation and before chemotherapy The microspheres of the present invention induce an initial increase in a patient having undergone radical mastectomy followed by radiation therapy.

Figure 12A:
Figure 12B:
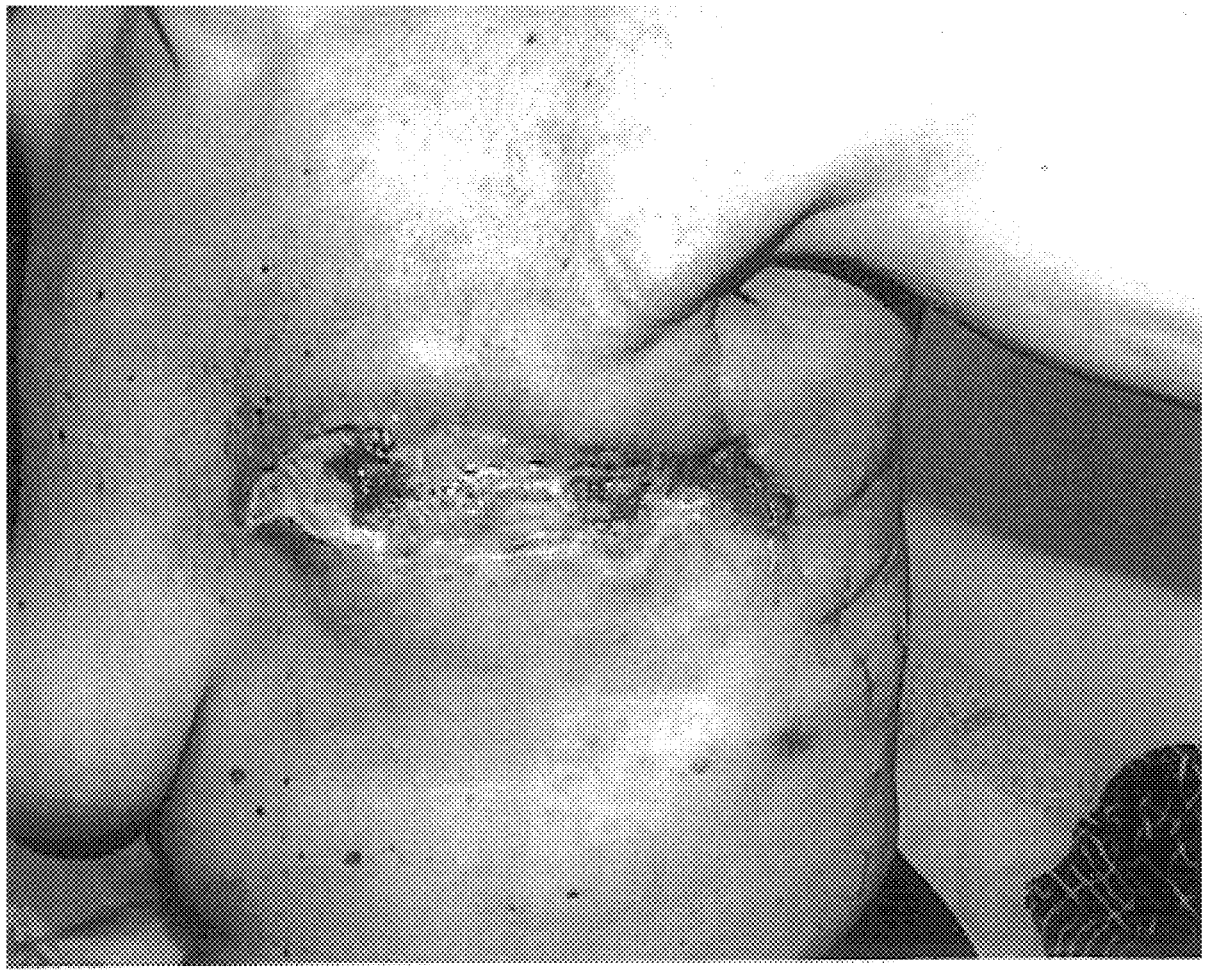
Figure 12C:
Figure 12D:

A fifty four year old breast cancer patient having stage II disease underwent surgery, followed by radiation therapy. The patient suffered from a necrotic lesion (FIG. 12A) and was advised not to have a course of chemotherapy to prevent the spread of her advanced disease, until the closure of necrotic wound was accomplished. The patient was treated with microspheres 2 times daily for 54 days. After 21 days of microsphere treatment, the patient's wound had improved and chemotherapy was started, until the closure of the wound was achieved. (FIG. 12B–12D). The patient was able to take a course of chemotherapy and is currently disease free. Thus, the composition of the present invention was useful in the treatment of wounds in combination with radiation therapy and chemotherapy.

Example 10

Microspheres Compositions in the Presence of Pharmacological Agents and Biologics In the following examples, the pharmacological agents and/or biologics are soluble in the pharmaceutical carrier but the microspheres are not and microspheres remain in suspension in the therapeutic composition.

a) A therapeutic composition made up of microspheres as described in Section 5.1 above, except that an antibiotic is added to the composition to prevent infections, for example, about 1–100 mg/ml neomycin sulfate, about 100–1000 Units/ml of bacitracin, about 10–100 mg/ml oxytetracycline HCL, or about 1–10 mg/ml gramacidin.

b) A therapeutic composition made up of microspheres as described in Section 5.1 above, except that a proteolytic enzyme is added to the composition to provide enzymatic debridement of pathogenic wounds when necessary, for example, about 10–100 units/ml of collagenase or elastase, about 10–100 units/ml of streptokinase or about 10–100 units/ml of streptodornase.

c) A therapeutic composition made up of microspheres as described in Section 5.1 above, except that an astringent is added to the composition to provide an emergency or battlefield therapeutic composition, for example, about 75–250 mg/ml of alum, about 100–1000 mg/ml of witch hazel, about 1–10% of povidine iodine, about 10–100 mg/ml ozone as an oxygen base or 10–100 mg/ml hydrogen peroxide.

d) A therapeutic composition made up of microspheres as described in Section 5.1 above, except a diamine is added to the composition to reduce collagen cross-linking, for example, about 1–50 mg/ml of putrescine, about 1–100 mg/ml of spermidine or about 1–150 mg/ml of cadaverine.

e) A therapeutic composition made up of microspheres as described in Section 5.1 above, except that a growth factor is added to the aqueous composition to enhance natural healing processes and stimulate growth, for example, about 10–100 units/ml of PGDF, PDAF, PDEGE or PF-4, about 10–100 units/ml of FGF, about 10–100 units/ml of EGF, about 10–100 units/ml of TGF, or about 10–100 units/ml of IGF.

f) A therapeutic composition made up of microspheres as described in Section 5.1 above, except an immune enhancer is added to the composition to stimulate the wound healing, for example, about 10–100 mg/ml L-arginine, about 5–50 mg/ml nitric oxide, about 50–500 mg/ml of quadrol, about 50–500 mg/ml of muramyl dipeptide, about 10–100 mg/ml of macrophage activating factor about 1–10 mg/ml of hyaluronic acid.

g) A therapeutic composition made up of microsphers as described in Section 5.1 above, except a metal ion is added to the composition, for example, about 1–10 mg/ml zinc chloride, about 1–10 mg/ml zinc gluconate, 1–100 mg/ml magnesium gluconate, about 1–10 mg/ml copper salts or peptides.

h) A therapeutic composition made up of microspheres as described in Section 5.1 above, except a vitamin is added to the composition, for example, about 100–10 units/ml vitamin A, about 50–500 mg/ml vitamin C or about 50–500 units/ml vitamin E.

i) A therapeutic composition made up of microspheres as described in Section 5.1 above, except an analgesic is added to the composition for treating trauma wounds encountered in emergency or battlefield, for example, about 5–50 mg/ml morphine sulfate, about 1–10 mg/ml fentamyl citrate or 5–50 mg/ml lidocaine hydrochloride.

j) A therapeutic composition made up of microspheres as described in Section 5.1 above, administered in combination therapy with radiation therapy, laser treatment, high pressure therapy or ozone.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying figures. Such modifications are intended to fall within the scope of the appended claims.

It is also to be understood that the following claims are intended to cover all of the generic and specific features of the invention herein described, and all statements of the scope of the invention which, as a matter of language, might be said to fall there between.

What is claimed is:

1. A therapeutic composition contained in a package for storing and mixing the composition from which the composition can be poured and applied on the surface of a wound, said composition comprising about 0.001–25% by weight of microspheres in suspension; said microspheres consisting essentially of a diameter in the range of 1.1 $\mu$m to 200 $\mu$m, said microspheres being capable of forming multipoint contacts with a cellular membrane and said microspheres being substantially non-biodegradable during the period of therapy; and a pharmaceutically acceptable carrier for said microspheres, said microspheres being substantially insoluble in said carrier.

2. The therapeutic composition as in claim 1, wherein the microspheres exhibit surface groups with a substantial charge.

3. The therapeutic composition as in claim 1, wherein said microspheres are made from a material selected form the group consisting of polystyrene, derivatized polystyrene, polylysine, poly-N-ethyl-4-vinyl-pyridinium bromide, polymethylacrylate and silicone.

4. The therapeutic composition as in claim 2, wherein said surface charge is substantially negative.

5. The therapeutic compositions as in claim 5, wherein said microspheres have a diameter in a range of from 2 μm to 100 μm.

6. The therapeutic composition as in claim 6, wherein said microspheres have a diameter in a range of from 1.1 μm to 20 μm.

7. The therapeutic composition as in claim 1, wherein said pharmaceutical carrier is selected from the group consisting of aqueous medium, aerosol carrier, aqueous solvent for pharmacological agents, aqueous solvent for biologics, ointment and bandage.

8. The therapeutic composition as in claim 1, further comprising an antibiotic.

9. The therapeutic composition as in claim 8, wherein said antibiotic is selected from the group consisting of tetracycline, oxytetracycline, gentamycin neomycin sulfate, bacitracin, polymyxin B sulfate and gramaciclin.

10. The therapeutic composition as in claim 1, further comprising a pharmaceutical agent.

11. The therapeutic composition as in claim 10, wherein said pharmaceutical agent comprises an antihistamine.

12. The therapeutic composition as in claim 10, wherein said pharmaceutical agent comprises and inflammatory agent.

13. The therapeutic composition as in claim 10, wherein said pharmaceutical agent is selected form the group consisting of an anticancer agent, an antiviral agent, and an antifungal agent.

14. The therapeutic composition as in claim 10, wherein said pharmaceutical agent comprises a metal ion.

15. The therapeutic composition as in claim 14, wherein said metal ion is selected from the group consisting of zinc, magnesium, cobalt, iron copper and manganese.

16. The therapeutic composition as in claim 10, wherein said pharmaceutical agent is an astringent.

17. The therapeutic composition as in claim 10, wherein said pharmaceutical agent is an anesthetic.

18. The therapeutic composition as in claim 1, further comprising a pharmacological agent which comprises an anesthetic selected from the group consisting of lidocaine, procaine and epinephrine.

19. The therapeutic composition as in claim 1, further comprising a pharmaceutical agent which is an analgesic.

20. The therapeutic composition as in claim 1, further comprising a pharmacological agent which comprises an analgesic consisting of morphine, heroin and fentanyl for treatment of pain.

21. The therapeutic composition as in claim 1, further comprising a pharmacological agent which is a cycloxygenase-2 inhibitor.

22. The therapeutic composition as in claim 1, further comprising a pharmacological agent which is a vitamin.

23. The therapeutic composition as in claim 1, further comprising a pharmacological agent which is an amino acid.

24. The therapeutic composition as in claim 1, further comprising a pharmacological agent which is a collagen.

25. The therapeutic composition as in claim 1, further comprising a growth factor.

26. The therapeutic composition as in claim 25, wherein the growth factor selected from the group consisting of PDGF, PDAF, PDEGF, TGFB, PF-4, αFGF, BFGF, GH, EGF AND IGF.

27. The therapeutic composition as in claim 25, wherein the biologic is a proteolytic enzyme.

28. The therapeutic composition as in claim 25, wherein the biologic is one or more stromal cells.

29. The therapeutic composition as in claim 25, wherein the biologic comprises an immune enhancer selected from the group consisting of L-arginine, nitric oxide, quadrol, muramyl dipeptide and other macrophage activating factors.

30. The therapeutic composition as in claim 25, wherein the biologic comprises hyaluronic acid for promoting the healing of surgical wounds, pathogenic wounds, bone fracture, stasis ulcers and chronic wounds.

31. A device comprising a container, said container holding the composition of claim 1.

* * * * *